(12) United States Patent
Rubbert

(10) Patent No.: US 8,454,362 B2
(45) Date of Patent: Jun. 4, 2013

(54) CUSTOMIZED DENTAL PROSTHESIS FOR PERIODONTAL- OR OSSEOINTEGRATION, AND RELATED SYSTEMS AND METHODS

(75) Inventor: Ruedger Rubbert, Berlin (DE)

(73) Assignee: Natural Dental Implants AG, Berlin (DE)

( * ) Notice: Subject to any disclaimer, the term of this patent is extended or adjusted under 35 U.S.C. 154(b) by 215 days.

(21) Appl. No.: 11/549,782

(22) Filed: Oct. 16, 2006

(65) Prior Publication Data
US 2008/0090208 A1 Apr. 17, 2008

(51) Int. Cl.
*A61C 8/00* (2006.01)

(52) U.S. Cl.
USPC .......................................... 433/173; 433/172

(58) Field of Classification Search
USPC ... 433/172–176, 201.1; 106/35; 523/115–118
See application file for complete search history.

(56) References Cited

U.S. PATENT DOCUMENTS

| | | | | |
|---|---|---|---|---|
| 2,721,387 A | * | 10/1955 | Ashuckian | 433/173 |
| 2,792,628 A | * | 5/1957 | Neumayer | 433/206 |
| 3,628,248 A | * | 12/1971 | Kroder et al. | 433/175 |
| 3,717,932 A | * | 2/1973 | Brainin | 433/175 |
| 3,984,914 A | * | 10/1976 | Schwartz | 433/201.1 |
| 4,178,686 A | * | 12/1979 | Riess et al. | 433/201.1 |
| 4,199,864 A | * | 4/1980 | Ashman | 433/175 |
| 4,278,630 A | | 7/1981 | Scheicher | |
| 4,504,229 A | | 3/1985 | Garito et al. | |
| 4,552,779 A | | 11/1985 | McClure | |
| 4,684,555 A | * | 8/1987 | Neumeyer | 433/202.1 |
| 4,828,117 A | * | 5/1989 | Panzera et al. | 206/63.5 |
| 5,002,488 A | * | 3/1991 | Homsy | 433/169 |
| 5,061,285 A | * | 10/1991 | Koch | 433/173 |
| 5,094,618 A | * | 3/1992 | Sullivan | 433/173 |
| 5,108,289 A | * | 4/1992 | Fukuyo | 433/173 |
| 5,123,844 A | * | 6/1992 | Wakai et al. | 433/201.1 |
| 5,264,215 A | * | 11/1993 | Nakabayashi et al. | 424/423 |
| 5,562,450 A | | 10/1996 | Gieloff et al. | |
| 5,691,905 A | | 11/1997 | Dehoff et al. | |
| 5,725,378 A | * | 3/1998 | Wang | 433/173 |
| 5,772,439 A | * | 6/1998 | Yamaoka et al. | 433/201.1 |

(Continued)

FOREIGN PATENT DOCUMENTS

| | | |
|---|---|---|
| CA | 2624830 A1 | 4/2007 |
| DE | 2729969 A1 | 1/1978 |

(Continued)

OTHER PUBLICATIONS

Apatite/Amelogenin Coating on titanium promotes osteogenic gene expression.*

(Continued)

*Primary Examiner* — Yogesh Patel
(74) *Attorney, Agent, or Firm* — Bracewell & Giuliani LLP

(57) ABSTRACT

A customized dental prosthesis for periodontal or osseointegration is disclosed having a manufactured implant portion shaped to substantially conform to the three-dimensional surface of a root of a tooth to be replaced. Furthermore a CAD/CAM based method of and a system for manufacturing a customized dental prosthesis replacing an extracted tooth is disclosed, where the extracted tooth is scanned regarding its three-dimensional shape and substantially copied using (a) an imaging system in-vitro like a 3D scanner or in-vivo like a cone beam CT system, (b) CNC machinery and (c) biocompatible material that is suitable to be integrated into the extraction socket and at least partially adopted by the existing tissue forming the socket.

25 Claims, 17 Drawing Sheets

U.S. PATENT DOCUMENTS

| | | | |
|---|---|---|---|
| 5,800,175 | A | 9/1998 | Zuk et al. |
| 5,921,778 | A | 7/1999 | Karmaker et al. |
| 6,089,867 | A * | 7/2000 | Filho .......................... 433/215 |
| 6,099,313 | A * | 8/2000 | Dorken et al. ................ 433/175 |
| 6,186,790 | B1 | 2/2001 | Karmaker et al. |
| 6,193,516 | B1 * | 2/2001 | Story ........................... 433/173 |
| 6,250,923 | B1 * | 6/2001 | Gibbs et al. .................. 433/173 |
| 6,436,143 | B1 * | 8/2002 | Ross et al. .................. 623/17.16 |
| 6,447,295 | B1 * | 9/2002 | Kumar et al. ................. 433/172 |
| 6,521,246 | B2 | 2/2003 | Sapieszko et al. |
| 6,534,197 | B2 * | 3/2003 | Noda et al. ................... 428/689 |
| 6,589,525 | B2 | 7/2003 | Gault |
| 6,696,073 | B2 | 2/2004 | Boyce et al. |
| 6,702,855 | B1 | 3/2004 | Steinemann et al. |
| 6,755,651 | B2 | 6/2004 | Brodbeck |
| 6,863,694 | B1 | 3/2005 | Boyce et al. |
| 6,913,666 | B1 | 7/2005 | Aeschlimann et al. |
| 6,921,264 | B2 | 7/2005 | Mayer et al. |
| 6,955,540 | B2 | 10/2005 | Mayer et al. |
| 6,984,261 | B2 * | 1/2006 | Cummings et al. ............. 106/35 |
| 7,008,226 | B2 | 3/2006 | Mayer et al. |
| 7,105,182 | B2 * | 9/2006 | Szymaitis ..................... 424/499 |
| 7,110,594 | B2 | 9/2006 | Jones et al. |
| 7,156,655 | B2 | 1/2007 | Sachdeva et al. |
| 7,234,937 | B2 | 6/2007 | Sachdeva et al. |
| 7,333,874 | B2 | 2/2008 | Taub et al. |
| 7,377,782 | B1 | 5/2008 | Brosnihan |
| 7,774,048 | B2 | 8/2010 | Nakaoka et al. |
| 2001/0055745 | A1 * | 12/2001 | Gault ........................... 433/201.1 |
| 2002/0102009 | A1 | 8/2002 | Jones et al. |
| 2003/0118968 | A1 * | 6/2003 | Massoud ....................... 433/173 |
| 2004/0015327 | A1 | 1/2004 | Sachdeva et al. |
| 2004/0038178 | A1 * | 2/2004 | Mayer et al. .................. 433/169 |
| 2004/0110110 | A1 | 6/2004 | Chishti et al. |
| 2004/0152034 | A1 * | 8/2004 | Cummings et al. ............... 433/8 |
| 2004/0197727 | A1 | 10/2004 | Sachdeva et al. |
| 2005/0033427 | A1 | 2/2005 | Freilich et al. |
| 2005/0038498 | A1 | 2/2005 | Dubrow et al. |
| 2005/0048440 | A1 * | 3/2005 | Feng ............................ 433/175 |
| 2005/0079469 | A1 * | 4/2005 | Akagawa et al. ............. 433/173 |
| 2005/0106534 | A1 * | 5/2005 | Gahlert ......................... 433/173 |
| 2005/0142517 | A1 | 6/2005 | Frysh et al. |
| 2005/0186540 | A1 | 8/2005 | Taub et al. |
| 2005/0260541 | A1 * | 11/2005 | McDevitt ..................... 433/173 |
| 2006/0003292 | A1 | 1/2006 | Lauren et al. |
| 2006/0078847 | A1 | 4/2006 | Kwan |
| 2006/0105295 | A1 * | 5/2006 | Mayer et al. .................. 433/173 |
| 2006/0154203 | A1 | 7/2006 | Emanuelli |
| 2007/0015110 | A1 * | 1/2007 | Zhang et al. .................. 433/173 |
| 2007/0072152 | A1 * | 3/2007 | Jaghab ........................... 433/215 |
| 2007/0264612 | A1 | 11/2007 | Mount |
| 2008/0090208 | A1 | 4/2008 | Rubbert |

FOREIGN PATENT DOCUMENTS

| | | |
|---|---|---|
| DE | 10020894 A1 | 11/2001 |
| DE | 10109118 A1 | 9/2002 |
| EP | 0 053 903 A1 | 6/1982 |
| EP | 0053903 B1 | 4/1987 |
| EP | 1073381 | 4/1999 |
| EP | 1150620 | 1/2000 |
| EP | 2087852 A1 | 8/2009 |
| EP | 2087853 | 8/2009 |
| EP | 2095789 | 9/2009 |
| JP | 95014400 B2 * | 2/1995 |
| WO | 0134056 A1 | 5/2001 |
| WO | 2004056405 A2 | 7/2004 |
| WO | WO-2004/056405 A2 | 7/2004 |
| WO | 2005057439 A1 | 6/2005 |
| WO | WO-2005/057439 A1 | 6/2005 |
| WO | 2005105164 A1 | 11/2005 |
| WO | 2006031096 A1 | 3/2006 |
| WO | WO-2006/031096 A1 | 3/2006 |
| WO | 2006060836 A1 | 6/2006 |
| WO | 2007006258 A1 | 1/2007 |
| WO | 2007125323 A1 | 1/2007 |
| WO | 2007038817 A | 4/2007 |
| WO | 2007038817 A1 | 4/2007 |
| WO | 2007131337 A1 | 11/2007 |
| WO | 2008017472 A2 | 2/2008 |
| WO | 2008047204 A3 | 4/2008 |
| WO | 2009020447 A1 | 2/2009 |

OTHER PUBLICATIONS

Exodontia: The Ogram System, pp. 1-2, Jan. 26, 2007.
Department of Dentistry : http://www.dent.ualberta.ca/, pp. 1, Jan. 26, 2007.
Emilio Nuzzolese et al., "Intentional Dental Reimplantation: A Case Report," The Journal of Contemporary Dental Practice, vol. 5, No. 3, Aug. 15, 2004, pp. 1-7.
Kevan Wong, "Exarticulation and reimplantation utilizing guided tissue regeneration: A case report," Quintessencce International, vol. 33, No. 2, 2002, pp. 101-109.
Albert C. Goerig et al., "Successful intentional reimplantation of mandibular molars," Quintessence International, vol. 19, No. 8, 1988, pp. 585-588.
Dean Benedict, "Reimplantation of Teeth," Quintessence International, Aug. 1980, pp. 41-47.
Kerr Corp., Datasheet, "Bioplant. Biocompatible, Synthetic, Osteoconductive," 2006.
Alex Touchstone et al., "Simplifying CAS/CAM Dentistry," Dental Products Report, Nov. 2005, An Advanstar Publication, pp. 1-20.
Iuxtaendo, Website Article re "Juxtaendo" Dentistry Implant (Antonio T. Di Giulio), downloaded from San Babila Day Hospital (Italy), Oct. 18, 2006.
El-Homsi, et al., Simulating Periodonal Effects in Dental Osseointegrated Implants: Effect of an Intramobile Damping Element on the Fatigue strength of Dental Implants—An in Vitro Test Method, Quintessence International, vol. 35, No. 6, 2004, pp. 449-455.
Mensor, et al., Compliant Keeper System Replication of the Periodontal Ligament Protective Damping Function for Implants, The Journal of Prosthetic Dentistry, Nov. 1998, vol. 80, No. 5, pp. 565-569.
Warrer, et al., Periodontal Ligament Formation Around Different Types of Dental Titanium Implants. I. The Self-Tapping Screw Type Implant System, J Periodontol, Jan. 1993, vol. 64, No. 1, pp. 29-34.
Malekzadeh, et al., Isolation of Human Osteoblast-Like Cells and In Vitro Amplification for Tissue Engineering, J Periodontol, Nov. 1998, vol. 69, No. 11, pp. 1256-1262.
Grzesik, et al., Cementum and Periodontal Wound Healing and Regeneration, Crit Rev Oral Biol Med, 2002, vol. 13, No. 6, pp. 474-484.
Buser, et al., Formation of a Periodontal Ligament Around Titanium Implants, J Periodontol, Sep. 1990, vol. 61, No. 9, pp. 597-601.
Bartold, et al., Tissue Engineering: A New Paradigm for Periodontal Regeneration Based on Molecular and Cell Biology, Periodontology 2000, vol. 24, pp. 253-269.
Van Dijk, et al., Cell-Seeding of Periodontal Ligament Fibroblasts, J Clin Periodontol, 1991, vol. 18, pp. 196-199.
Lang, et al., Attachment Formation Following Replantation of Cultured Cells into Periodontal Defects—a Study in Minipigs, J Dent Res, Feb. 1998, vol. 77, No. 2, pp. 393-405.
Lin, et al., Dental Implants with the Periodontium: A New Approach for the Restoration of Missing Teeth, Elsevier, Medical Hypotheses, 2009, vol. 72, pp. 58-61.
Reichert et al., Tuning Cell Adhesion on PTFE Surfaces by Laser Induced Microstructures, Advanced Engineering Materials, 2007, vol. 9, No. 12, Wiley-VCH Verlag GmbH & Co. KGaA, Weinheim, pp. 1104-1113.
International Preliminary Examination Report for PCT/IB2007/003072 dated Apr. 22, 2009, 12 pages.
Partial File History for co-pending U.S. Appl. No. 11/724,261, filed Mar. 15, 2007.
Patient Information Leaflet Orthognathic Surgery, British Orthodontic Society, 2 pages.
Metzger, et al., Manufacturing Splints for Orthognathic Surgery Using a Three-Dimensional Printer, http://www.aadmrt.com/currents/metzgeretal_winter_09_print.htm, Apr. 8, 2009, 14 pages.
International Search Report dated Jul. 22, 2008, 9 pages.

Written Opinion of the International Searching Authority dated Apr. 16, 2009, 13 pages.
Abstract for WO2007038817, esp@ce.net, 1 page.
European Search Report for Application No. 09075153.8 dated Jun. 29, 2009, 7 pages.
European Search Report for Application No. 09075155.3 dated Jun. 29, 2009, 7 pages.
Partial File History for U.S. Appl. No. 11/724,261.
Arthur Veis, et al., "Specific Amelogenin Gene Splice Products Have Signaling Effects on Cells in Culture and in Implants in Vivo", The Journal of Biological Chemistry, 2000 by The American Society for Biochemistry and Molecular Biology, Inc., vol. 275, No. 52, pp. 41263-41272, Dec. 29, 2000.
Fumi Kawana, et al., "Porcine Enamel Matrix Derivative Enhances Trabecular Bone Regeneration During Wound Healing of Injured Rat Femur", The Anatomical Record, 2001, vol. 264, pp. 438-446.
Mayumi Iijima, et al., "Control of octacalcium phosphate and apatite crystal growth by amelogenin matrices", Journal of Materials Chemistry, 2004, vol. 14, pp. 2189-2199.
A.M. Hoang, et al., "Amelogenin is a Cell Adhesion Protein", Journal of Dental Research, 2000, http://www.sagepublications.com, vol. 81 (7), pp. 497-500.
L. Hammarstrom, et al., "Periodontal regeneration in a buccal dehiscence model in monkeys after application of enamel matrix proteins", Journal of Clinical Periodontology, 1997, vol. 24, pp. 669-677.
B.D. Boyan, et al., "Porcine Fetal Enamel Matrix Derivative Enhances Bone Formation Induced by Demineralized Freeze Dried Bone Allograft In Vivo", J. Periodontal, 2000, vol. 71, No. 8, pp. 1278-1286.
A. Veis, "Amelogenin gene splice products: potential signaling molecules", CMLS Cellular and Molecular Life Sciences, Birkhauser Verlag, Basel, vol. 60 (2003) pp. 38-55.
Frank Schwarz, et al., "Effect of enamel matrix protein derivative on the attachment, proliferation, and viability of human Sa0s2 osteoblasts on titanium implants", Clin Oral Invest, Springer-Verlag (2004), vol. 8, pp. 165-171.
Kevin Tompkins, et al., "Two Related Low Molecular Mass Polypeptide Isoforms of Amelogenin Have Distinct Activities in Mouse Tooth Germ Differentiation in Vitro", Journal of Bone and Mineral Research, vol. 20, No. 2, 2005, pp. 341-349.
H.B. Wen, et al., "Modulation of apatite crystal growth on bioglass by recombinant amelogenin", Biomaterials, vol. 20, (1999) pp. 1717-1725.
H.B. Wen, et al., "Modification of calcium-phosphate coatings on titanium by recombinant amelogenin", Center for Craniofacial Molecular Biology, School of Dentistry, Univ. of Southern California, 2003 Wiley Periodicals, Inc., pp. 483-490.
L. Heijl, Periodontal regeneration with enamel matrix derivative in one human experimental defect; Journal of Clinical Periodontology, 1997, vol. 24, pp. 693-696.
A.G. Fincham, et al., "The Structural Biology of the Developing Dental Enamel Matrix", Journal of Structural Biology, 1999, vol. 126, pp. 270-299.
Chang Du et al., "Supamolecular Assembly of Amelogenin Nanospheres into Birefringent Microribbons", Science, 2005, vol. 307, pp. 1450-1454.
Straumann; Emdogain, "The reliable solution for periodontal treatment," www.straumann.com, Mar. 2006.
European Search Report for Application No. 09075154.6, dated Jul. 13, 2009, 7 pages.
Partial File History of U.S. Appl. No. 11/562,953 {Hall), filed Nov. 22, 2006.
"Materialise Scores Against Nobel Biocare: More Changes Looming in the Surgical Guide Market?", http://www.osseonews.com/materialise-against-nobel-biocare/print/[Oct. 17, 2011 7:41:51 PM].
Ganz, Use of Stereolithographic Models as Diagnostic and restorative Aids for predictable Immediate Loading of Implants, 15(10) Pract. Proced. Aesthet. Dent. (2003), pp. 763-771.
Dakhno, Abstract—"Maxillolofacial surgery planning for the insertion of dental implants obtained from CT data using the SimPlant interactive software", 2(2) Implantology & Paradontology & Osteology (2005), pp. 23-27.
Mupparapu, "Implant Imaging for the Dentist", 70(1) J. Canadian Dent. Assoc. (2004), pp. 32-32g.
European Search Report for Application No. 09075154.6, dated Jul. 13, 2009.
European Search Report for EP Application No. 09075153.8, dated Jul. 8, 2009.
European Search Report for EP Application No. 09075155.3, dated Jul. 29, 2009.
Int'l Prelim. Rpt. on Patentability and Written Opinion for PCT/IB2007/003072, dated Apr. 22, 2009.
Partial File History of U.S. Appl. No. 12/763,001, filed Apr. 19, 2010.
Partial File History of U.S. Appl. No. 13/247,607, filed Sep. 28, 2011.
Non-final Office Action, dated Sep. 17, 2012 from co-pending U.S. Appl. No. 12/763,001.

* cited by examiner

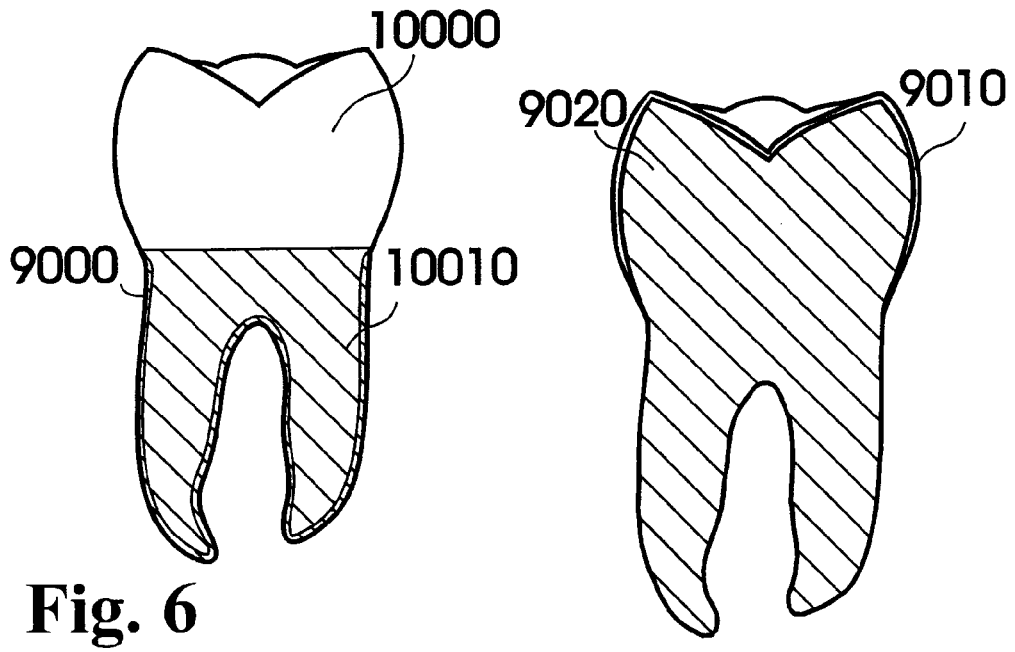
Fig. 6
Fig. 7
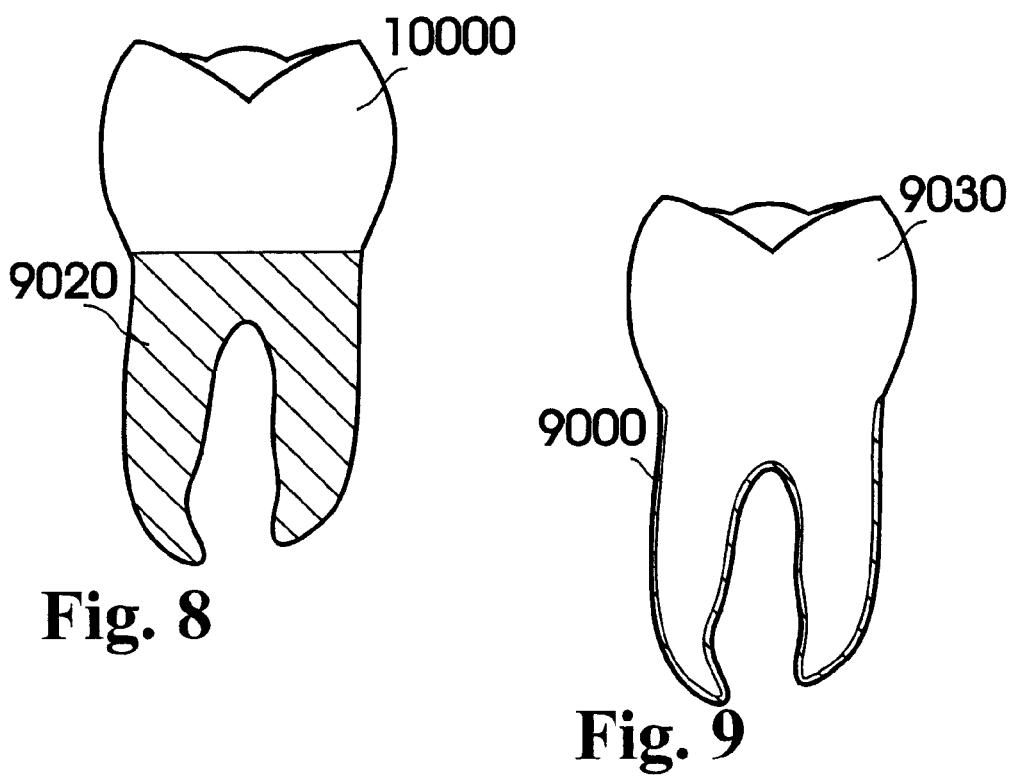
Fig. 8
Fig. 9

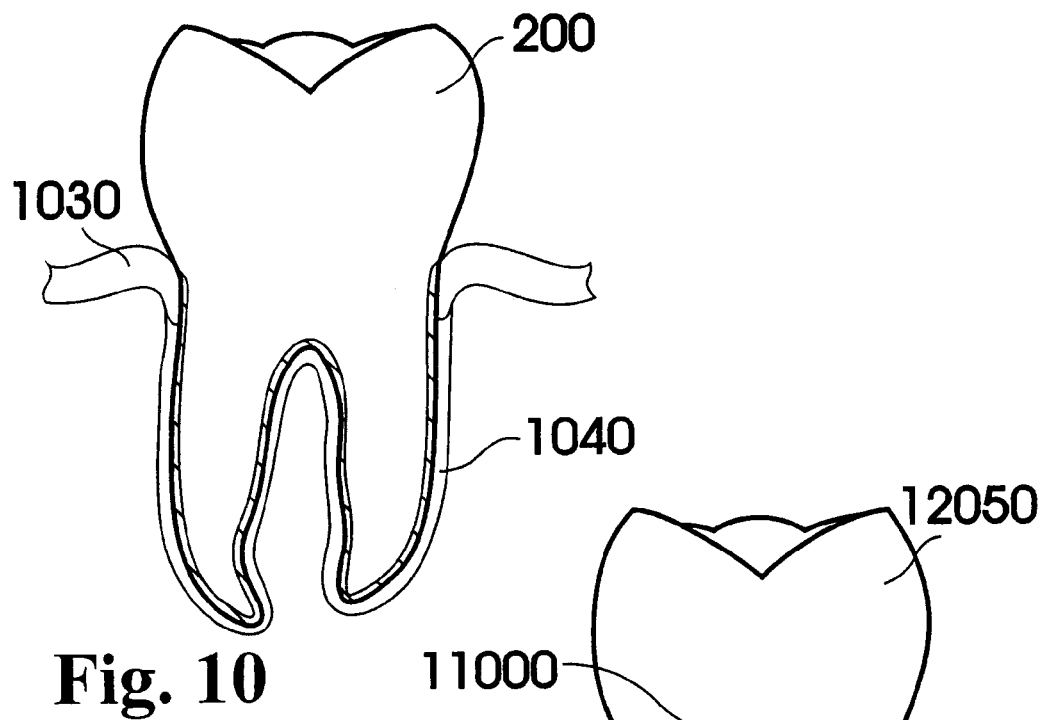
Fig. 10
Fig. 11
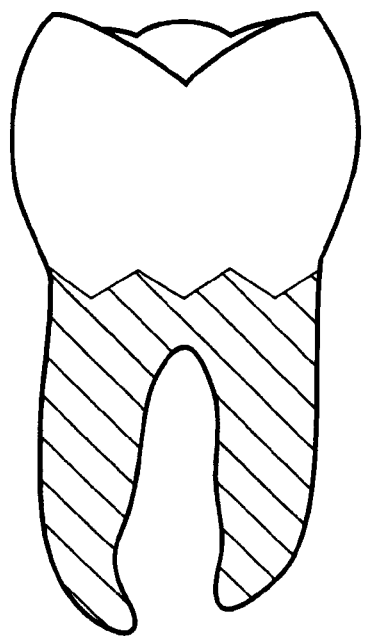
Fig. 12

```
solid MYSOLID
  facet normal  -0.470578   -0.335539    0.816070
    outer loop
      vertex    0.000000E+00 -12.5120    1.76950
      vertex    0.460000E-02 -11.7876    2.07000
      vertex   -1.78420     -11.8027    1.03230
    endloop
  endfacet
  facet normal  -0.470359   -0.336719   -0.815710
    outer loop
      vertex   -1.53240     -12.5120   -0.884700
      vertex   -1.78420     -11.8027   -1.03230
      vertex    0.460000E-02 -11.7876   -2.07000
    endloop
  endfacet
  facet normal   0.939923   -0.341387    0.000000E+00
    outer loop
      vertex    1.53240     -12.5120   -0.884700
      vertex    1.80230     -11.7689   -1.03730
      vertex    1.80230     -11.7689    1.03730
    endloop
  endfacet
  facet normal   0.414021   -0.560697    0.717081
    outer loop
      vertex    1.80230     -11.7689    1.03730
      vertex    2.47780     -10.5144    1.62820
      vertex   -0.342400    -10.5144    3.25650
    endloop
  endfacet
```

Fig. 32

```
%PRG001
N10  G17 G40 G90 T11 F6000 S12000
N20  G00 X-20 Y0 Z50
N30  G01 X-20 Y0 Z-5
N40  G01 X600 Y0 Z-5
N50  G03 X600 Y400 I600 J200 Z-5 F2000
N60  G01 X300 Y400 Z-5 F6000
N70  G01 X300 Y300 Z-5
N80  G01 X0 Y300 Z-5
N80  G01 X0 Y-20 Z-5
N100 G01 X0 Y-20 Z50
N110
.
.
.
Nxxx M30
```

Fig. 33

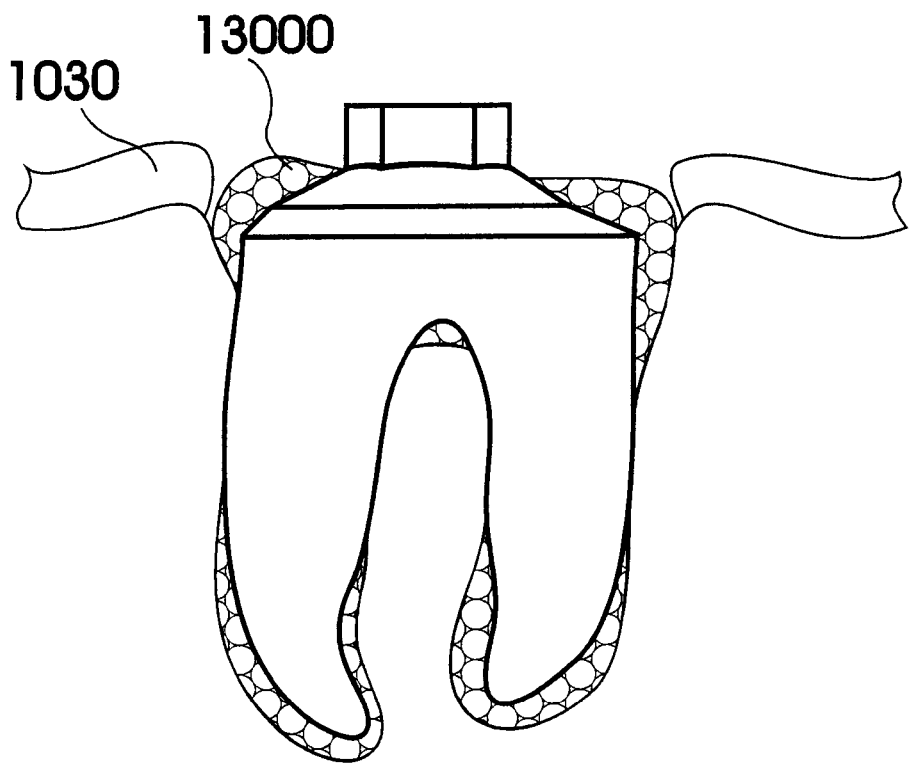

Fig. 34

CUSTOMIZED DENTAL PROSTHESIS FOR PERIODONTAL- OR OSSEOINTEGRATION, AND RELATED SYSTEMS AND METHODS

FIELD OF THE INVENTION

The invention relates generally to the field of dentistry, and more particularly to the field of dental restorations, implants and prostheses. The invention further relates to computer assisted and conventional systems and methods for designing and manufacturing such custom dental prosthesis.

BACKGROUND OF THE INVENTION

Human teeth serve a variety of functions. Not only are they important for chewing food, but they also necessary to pronounce certain consonants properly, especially fizzle- and S-sounds. Furthermore, teeth play a major role in our personal appearance. White, healthy and well aligned teeth are an ideal of beauty and appear as a cosmetic sign of youth and success.

Although various preventive measures, like frequent tooth brushing and flossing, and drinking fluoridized or iodized water are widely accepted and used, the great majority of people sooner or later challenged with dental fillings, restorations implants, and/or prostheses.

The major goal in dentistry is to postpone loss of teeth as long as possible. Another goal is certainly to provide comfortable prostheses with a broad scope/indication and a long lasting life-time.

Generally, the number of available restorative and prosthetic options is limited. Typically fillings, inlays, and crowns are used if the root and its embedding periodontal structure are healthy, and sufficient as support for such restorative partial prostheses. Traditionally, if the original tooth can no longer be used; the use of bridges or non-customized osseointegrated implants is indicated. In this context, several negative aspects are to be endured. In order to provide the support structure for a bridge, adjacent teeth are ground, and healthy enamel is partially destroyed. Osseointegrated implants are drastically invasive and the gingiva-implant interface is often the cause of chronic local infection. Additionally, all the aforementioned restorative and prosthetic options have a limited average lifetime. Removable dentures are certainly the final prosthetic option.

When a tooth is partially damaged, either by caries or mechanical impact, the missing portion should in most cases be replaced. As long as a tooth provides enough structural strength to support a prosthesis, for example, an inlay or a crown, this will typically be the preferred solution. However, if the loss of tooth substance is severe, this may not be applicable. In these cases, a bridge can be applied, enduring the aforementioned negative consequences. Another option is to replace the tooth with an implant.

There are many methods or options for replacing missing teeth. Off-the-shelf or pre-shaped osseointegrated dental implants are one of the options. Osseointegration means the direct contact of the implant surface with the bone without a fibrous connective tissue interface (natural teeth are typically not in direct contact with the bone, but are connected to the bone by ligaments). The use of such dental implants includes a wide variety of implant designs and materials, use of implants in different locations in the mouth and use of a variety of surgical protocols.

Endosteal implants are placed into the bone, like natural tooth roots. They can provide an anchor for one or more artificial teeth. They are the most commonly used type of implants. There are various types of endosteal implants, for example, screws, cylinders, and blades.

Subperiosteal implants are implants that are placed over the bone in cases where the bone has atrophied and jaw structure is limited. Subperiosteal implants are customized metal frameworks, providing the equivalent of multiple tooth roots. They can be applied in a limited area or in the entire mouth. After application, natural tissue membrane or bone will grow back around the implant, thus providing more stability. Posts protrude through the gum to hold the prosthesis.

Traditionally, osseointegrated dental implants are placed in bone and covered by mucosa during the immediate postoperative healing period. At four to eight months, a second surgical procedure is performed to expose the implant so it may be loaded with various types of dental crowns. In recent years, immediate implant placement following tooth extraction and immediate crown loading after surgical placement has become more common.

However, the success rate and the in-vivo life time of osseointegrated dental implants are limited, and the surgical procedure is heavily invasive, because the bone needs to be drilled or ground in order to be adapted to the shape of the non-customized implants. Furthermore, osseointegrated implants are a limiting factor in a later orthodontic treatment. Problems relating to nerve transposition, osseous grafting, ridge augmentation, and sinus augmentation of osseointegrated dental implants, and/or to tissue health adjacent to dental implants have also been reported. Patients often complain about chronically infected periodontal structure caused by osseointegrated implants.

In cases where a tooth is not severely damaged, and would be ready to receive a partial restoration, but an intra-oral repair is impossible due to access problems, or a reverse root canal treatment is required, an alternative method is the intentional re-implantation. The tooth is extracted, repaired, and re-integrated into the existing periodontal structure of a dental patient. Nuzzolese et al write in the Journal of Contemporary Dental Practice, Volume 5, No. 3, Aug. 15, 2004: "It is well known dental reimplantation is indicated following traumatic avulsion by the preservation of cellular vitality in the periodontal ligament and under conditions of asepsis. The rate of endodontic success at five years reported in the literature ranges between 70% and 91%. However, intentional dental reimplantation is an effective strategy for the treatment of teeth that would be difficult, if not impossible, to treat using traditional root canal therapy. Different prognoses exist for intentional dental reimplantation and trauma-related reimplantation. This is due to such important variables such as the level of cellular vitality in the periodontal ligament; the degree of trauma to surrounding tissues, and the degree of asepsis when a tooth is removed. Surgical extraction is more favorable in this regard compared to a traumatic avulsion scenario." Although this method is not yet widely used, the reported success rates are noteworthy. A disadvantage is certainly that the specific tooth still needs an overall reasonable condition and prognosis to justify an intentional re-implantation and that only certain root and root canal deficiencies can be repaired this way.

Various publications reporting that the prognosis of intentional reimplanted or transplanted teeth is significantly better than the reimplantation after a traumatic extraction, since the extraction is surgically controlled and relatively aseptic techniques are utilized. Spouge writes in his Oral Pathology, Mosby, Saint Louis 1973; "The majority of reimplantations however are clinically successful, and the teeth are retained firmly in the socket for the appropriate 5 year period. However, despite the apparent success, most of them show localized ankylosis and gross resorption of the root at the end of this time. The fibrous attachment that develops in the new periodontal ligament area often involves the formation of an immature type of connective tissue whose fibers remain tangential to the root surface rather than becoming physiologically oriented. There is experimental evidence to suggest that formation of a physiologic periodontium is more easily achieved in condition where the viability of the original periodontal ligament is maintained . . . . In keeping with this, the prognosis for clinical successin a reimplanted tooth fall rapidly if is have been completely dislocated from its socket for more than 24 hours." Wong suggests in Quintessence International, Vol. 33. No. 2, 2002 a surgical "exarticulation" method, where the removal of the tooth from its socket is achieved "(after the incision of the crestal periodontal ligament fibers with micro-blades) with a combination of luxation and gentle, rotary, reciprocating movements" in order to minimize physical trauma to the excising periodontium. Goerig et al recommends in Quintessence International, Vol. 19, No. 8, 1988 a sectioning procedure where a molar tooth is cut in half dividing the roots in order to minimize the damage of the existing periodontal ligament.

All such restorative and prosthetic options and methodologies are deficient being heavily invasive and limited in their respective scope. There has not been recognition, until now by the Applicant, of the need for a product, systems, and methods related to the integration of dental prosthesis such as artificial tooth, bridges, or segments of the dentition that includes custom-shaped root structures to be osseointegrated or even more beneficial integrated into the existing periodontal structure of an individual patient, having the desirable broad scope and reduced invasive requirements.

The product, and related systems and methods provided by the present invention comprise several independent inventive features providing substantial improvements to prior art. The greatest benefit will be achieved for dental treatments especially for patients requiring tooth replacement.

SUMMARY OF THE INVENTION

In view of the foregoing, embodiments of the present invention beneficially provide a customized dental prosthesis and implant in various embodiments based on a process that includes copying a significant portion of the original root geometry of a human tooth, to be integrated after extraction of the original tooth either in the existing biological cell structure of the periodontal ligament or into the embedding bone structure of the respective jaw. The concept of periodontal integration of an artificial tooth uses the existing human periodontal ligament for integration and is certainly less invasive than the integration of osseointegrated implants. The various embodiments of this invention are not only substitutive but additive to the available options in the field of restorative and prosthetic dentistry with the result that in most cases the need to use removable dentures will be significantly postponed.

In this context, the invention described herein relates to fabricating customized segments of the dentition, single teeth, roots and crowns or parts of those. The artificial reproduction of the original root will be inserted into the alveolus, the natural cavity of the root of the tooth to be replaced. It will either be adopted by the periodontal ligament of the patient or osseointegrated, if the periodontal ligament is no longer functional. The shape of the root will be a substantial copy of the root to be replaced or may be intentionally smaller for example to compensate for measurement or manufacturing tolerances or inaccuracies. The shape of such roots may be a copy of the root to be replaced, or it may be adapted to the alveolar situation. In certain cases it is adventurous according to the invention to modify the shape to be integrated. For instance it may be appropriate to conjoin the two or three roots of a molar to gain additional stability or enable the manufacturing of such. Also, strongly bent root tips may be reduced or left away in order to ease the insertion of the prosthesis.

The invention avoids or postpones the need of conventional heavily invasive implants for a significant time by using at first the natural periodontal structure as long as possible and afterwards by customized osseointegrated artificial roots or teeth.

No approach in dentistry based on design and manufacture of customized teeth including the root, or only roots suitable to be used in conjunction with off-the-shelf or customized components (typically for the visible part like veneers or complete crowns) used in the field of implantology for an individual patient, and design and manufacture of such customized tooth, has been proposed up to date. The implants widely used in dental treatment today are off-the-shelf products. Because teeth have to fit properly for comfort and healing-process after surgery in the periodontal ligament of a patient, some commonly used implants do not constitute an optimal replacement.

In an embodiment of the invention disclosed herein the artificial root will be osseointegrated. It will be embedded into the natural extraction cavity.

Another embodiment of the present invention maintains and preserves the principle of the natural mechanism of holding the teeth in the jaw structure of a dental patient in cases where a tooth needs to be replaced. The customized dental prostheses are integrated into, healed in, and at least partially adopted by the fibrous connective tissue interface of the anatomical structure of an individual patient that is naturally holding the tooth.

Directly after placement, the prosthesis needs to be tied, glued or otherwise fixated for several weeks to adjacent original or artificial teeth or tentative implants like mini-screws.

BRIEF DESCRIPTION OF THE DRAWINGS

Embodiments of the invention are described below in conjunction with the appended drawing figures, where like reference numerals refer to like elements in the various views, and wherein:

FIG. 6 shows an artificial tooth having a root portion and a crown portion, the portions representing the root being coated in order to promote periodontal integration.

FIG. 7 is a view of an artificial tooth being made from a material promoting periodontal integration, the crown being coated with another material having optimized esthetic and/or mechanical properties.

FIG. 8 shows an artificial tooth, the portion representing the crown being made from a material having optimized esthetic and/or mechanical properties, while the portion representing the root is made from a material promoting periodontal integration.

FIG. 9 is a view of an artificial tooth being made from a material having optimized esthetic and/or mechanical properties, the portions representing the root being coated in order to promote periodontal integration.

FIG. 10 shows an artificial tooth being embedded in the socket of the natural tooth.

FIG. 11 shows a view of a segmented artificial tooth, the segment representing the root being connected to the segment representing the crown by a connecting element.

FIG. 12 is a view of a segmented artificial tooth, the segment representing the root and the segment representing the crown having an interlocking connection.

FIG. 32 shows an arbitrary portion of an STL file in ACSII format.

FIG. 33 shows an arbitrary portion of an IGES file in ACSII format.

FIG. 34 shows an implanted artificial tooth, the voids between the root portion and the extraction socket filled with a bone promoting substance.

DETAILED DESCRIPTION OF EMBODIMENTS

The present invention will now be described more fully hereinafter with reference to the accompanying drawings, which illustrate embodiments of the invention. The invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
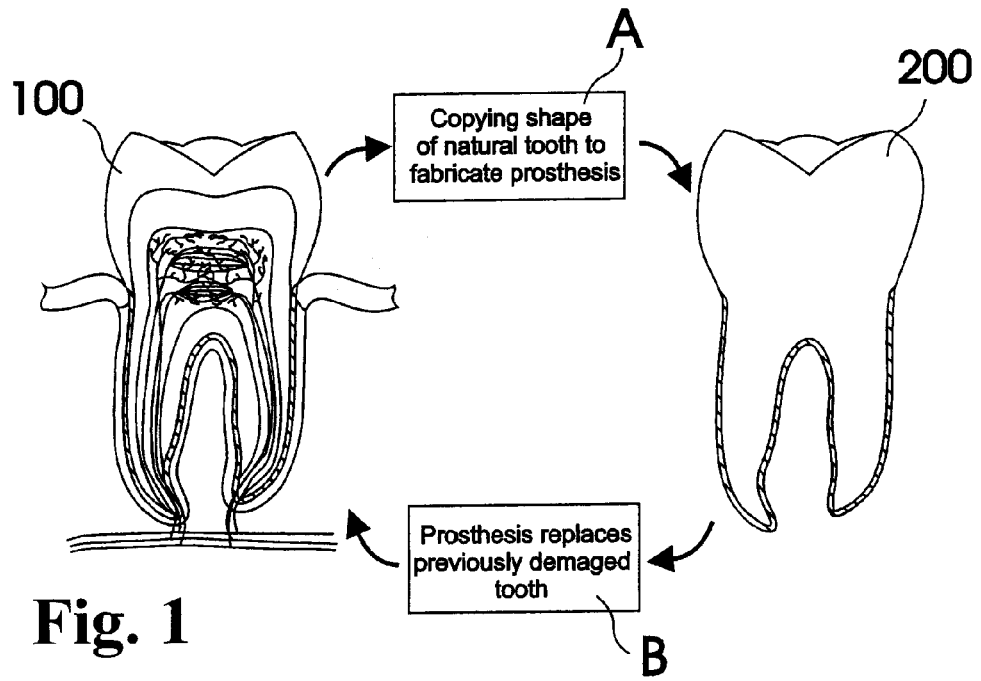
FIG. 1 shows a procedure of replacing a human tooth with a prosthesis in accordance with an aspect of the invention.
Figure 28:
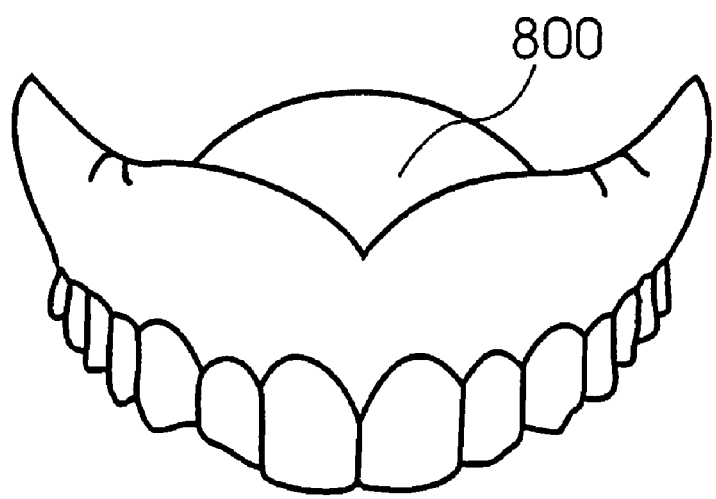
FIG. 28 shows a removable denture according to prior art.

Current methods for replacing damaged teeth have several disadvantages. For example, conventional bridge implants require healthy teeth to be ground, and osseointegrated implants are drastically invasive. Additionally, these prostheses have a limited average lifetime. Removable dentures (800) as shown in FIG. 28 are certainly the final prosthetic option. An object of the invention is to design and manufacture customized dental prosthesis for replacing human teeth. FIG. 1 illustrates a method of replacing a human tooth with a customized dental prosthesis according to an embodiment of the invention. First, in step (A) a copy (200) of the natural tooth (100) to be replaced is fabricated. Then, in step (B) the natural tooth (100) is replaced with the prosthesis (200).

Figure 2:
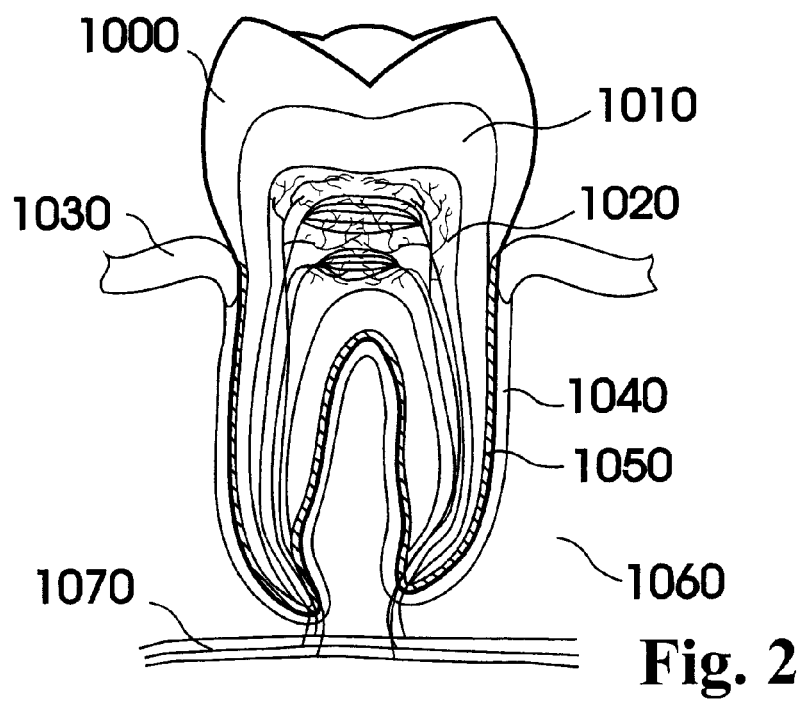
FIG. 2 is a detailed cross-sectional view of a natural tooth.

FIG. 2 shows a natural tooth embedded in its socket. The pulp (1020) holds nerves and blood vessels (1070). It is surrounded by dentine (1010), which is covered with enamel (1000). The root portions have a thin layer of cementum (1050) providing connection to the ligament (1040), which serves to anchor the tooth to the bone (1060). The outside of the bone is covered with gum (1030).

Figure 26:
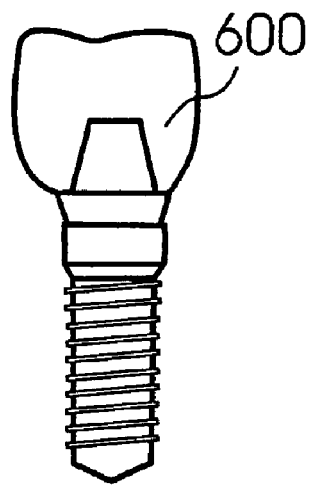
FIG. 26 shows a dental implant according to prior art
Figure 27:
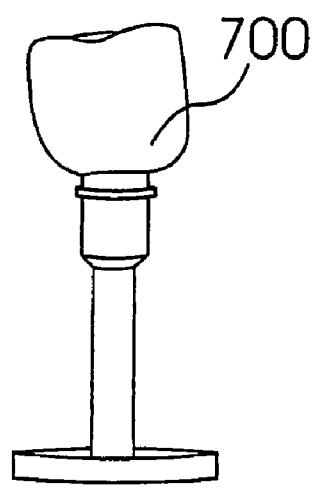
FIG. 27 shows another implant according to prior art.

FIGS. 26 and 27 show conventional implants. The implanted portion (610 and 710) is an off-the-shelf part to be inserted into a hole drilled into the jaw bone. The crown (600 and 700) is generally customized to the individual tooth it is replacing.

According to an embodiment of invention, a dental prosthesis is individually shaped and integrated into the natural extraction socket of an individual patient. The shape of the portions of the prosthesis representing the root substantially copies the natural root of the tooth that was located in the socket. However, the shape may be modified in order better adapt to the natural socket or to ease insertion of the prosthesis. Also, the socket may be surgically adapted for the same reasons. According to the invention, a segmented prosthesis can be used. A segmented, also referred to a segment, prosthesis is one in which a first segment is implanted into the extraction socket and second segment, for example, a portion representing the crown of a tooth is attached to the segmented portion. Accordingly, segment prosthesis includes at least two separate portions which may be manufactured and implanted at separate times. The segment which is implanted into the extraction socket is a representation of the root of the natural tooth and can be manufactured based on 3D imaging data. The segment representing the crown can be manufactured according to standard procedures known in the art.

The invention comprises the following steps: (i) Recording and digitizing (scanning) the three-dimensional anatomical shape of a human tooth or dentition; (ii) Obtaining a virtual model of the tooth as data record; and (iii) Manufacturing of the prosthesis, bases on the three-dimensional data that have been obtained by the scan and—if applicable—optimized.

The data may either be recorded intra-orally from the patient, such as with a 3D camera, a micro laser optical device, a computerized tomography apparatus, or an ultrasound apparatus, or be recorded extra-orally by scanning an extracted tooth. If required, the model can be modified in order to ease insertion or to receive aids for the final correct positioning of the fabricated prosthesis. The prosthesis can be directly produced by milling, grinding or rapid prototyping, for example, at a dentist's office or in a laboratory. It can also be produced using conventional laboratory procedures like casting. Preferably, the implant portion representing the root is manufactured using CAM methods, based on an acquired virtual model, while other portions of the prosthesis, for example, representing the crown, or bridge, are manufactured using standard procedures known in the art.

The process of milling or grinding dental crowns and inlays from ceramic material based on digital data was successfully introduced to dentistry approximately twenty years ago by SIEMENS (now Sirona, Bensheim, Germany) under the brand name CEREC. A modification of the SEREC system as would occur to one of ordinary skill of the use of suitable similar CAD/CAM and CNC design and manufacture as would occur to one of ordinary skill in the art. Although conventional prosthesis manufacturing systems, such as the CEREC system, are generally closed systems, one skilled in the art would readily appreciate these closed systems can be modified such that they may be readily integrated into the methods of the invention. Furthermore, certain embodiments of the invention disclosed herein relate to standard off-the-shelf CAD/CAM and CNC components that can be readily integrated into the disclosed methods Preferably, at least the customized implant portion of the dental prosthesis is fabricated using a CAD/CAM based method and system, wherein, the three-dimensional shape of an extracted tooth is scanned and substantially copied, using a 3D scanner, multi-axes CNC machinery and biocompatible material or material later to be covered with a thin layer of biocompatible material that is suitable to be integrated into and adopted by the existing periodontal ligament cell structure of an individual patient.

Figure 5:
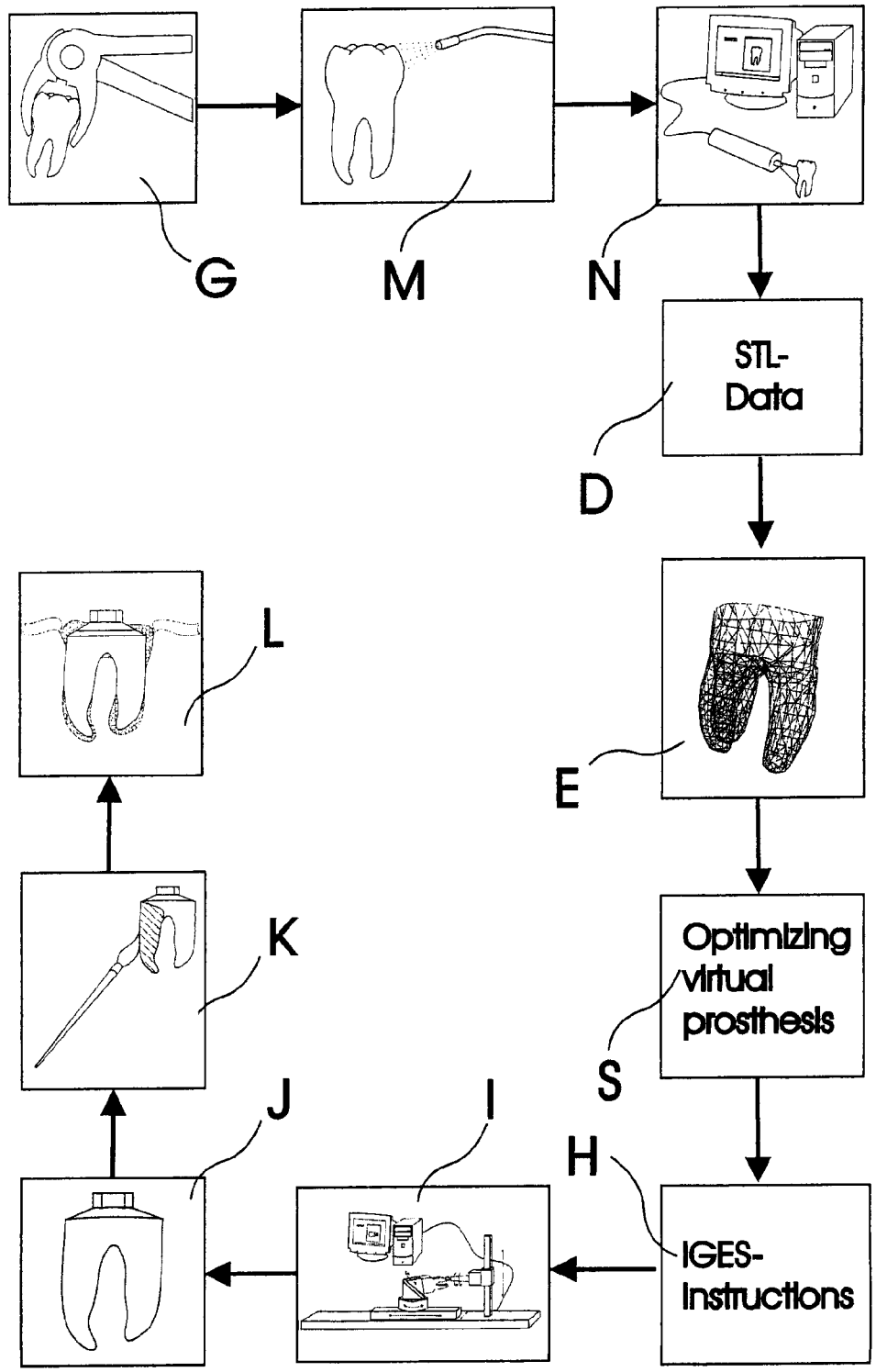
FIG. 5 shows the process steps of acquiring three-dimensional data of the root of an extracted human tooth, processing and completing the resulting 3D data with features for connecting an off-the-shelf abutment and inserting the prosthesis into the socket of the natural tooth according to an embodiment of the invention.

An overview of a method for replacing a tooth according to the invention is shown in FIG. 5. First, the tooth to be replaced is extracted (step G) and properly cleaned (step M). Then 3D imaging (step N) is performed in order to obtain 3D data (D) representing the three-dimensional shape of the root of the tooth. The resulting 3D data is imported into CAD software and displayed to an operator (step E). At this point, the 3D data may be modified, for example, to alter the shape of the root of the virtual model. It should be noted that FIG. 5 contemplates possibly interaction with an operator, one skilled in the art would readily appreciate that this functionality may be fully automated. Additional features may be added from a digital library and merged into the 3D root data (step S). The resulting 3D data is converted into IGES format and exported (step H) to a CAM system for fabricating (step I) the prosthesis (J). The fabricated prosthesis is then coated with a substance promoting bone ingrowth (step K). It should be noted that coating the prosthesis is an optional step. The prosthesis is then implanted into the extraction socket (step L).

The tooth to be replaced, for instance a lower left incisor (having an envelope volume of approximately 7 mm×8 mm×23 mm) is extracted in a surgical environment, then disinfected and cleaned in a solution of hydrogen peroxide. The three-dimensional shape (scanning) of the extracted tooth may be obtained using, for example, a light-based scanner like ATOS II SO (gom GmbH, Braunschweig, Germany). In a first step, the root of the tooth is scanned. To achieve an optimal surface for optical scanning, the root is covered with a thin layer of $TiO_2$ powder (like CEREC powder from Sirona, Bensheim, Germany) that is applied with an atomizer using compressed air. Other coatings are also applicable that can for instance be applied by air-brush painting or a regular brush. For example it is possible to "shake-up" $TiO_2$ powder in alcohol applying a uniform thin layer of $TiO_2$ by airbrushing generating this way high-precision data during scanning. A portion of the crown of the tooth is attached to the turntable of the scanner using a removable adhesive material (like for instance wax used in dental laboratories).

The turntable is then rotated in 15° increments step by step for a 360° view. The scanner scans at each of the 15° degree increments the optically accessible root surface of the tooth and is thus generating and exporting digital surface data representing the scanned portions of the three-dimensional shape of the surface of the root. The turntable is controlled by the software delivered with the scanner.

The digital surface data consists of multiple measurement data points each having an x, y, and z coordinate and together having a density better than 0.1 mm and an accuracy noise of less than 0.05 mm. Alternatively other resolutions, accuracies, and coordinate systems including but not limited to cylindrical or spherical coordinate systems can be employed by those skilled in the art. The data points are exported in STL format. This widely used file format describes a surface or portions of a surface by interconnected triangles. STL files can be encoded either binary or in ASCII format. FIG. 32 shows an arbitrary example of a portion of such a file in the easily readable ASCII format.

Reference elements that are fixed to the turntable are additionally scanned at each increment. The ATOS II scanner software is able to detect such reference elements in the STL data of each incremental scan. Based on the reference elements it automatically transforms, superimposes and combines the incremental scans. The result is a comprehensive STL file describing the surface of the root of the tooth.

Other suitable imaging methods include but are not limited to CT, CBCT, MRT, ultra sound, destructive scanning, active triangulation, passive triangulation, confocal scanning, and TOF (Time Of Flight). Such methods are generating either surface descriptions for example in STL-format or volumetric data for example in a so called "voxel"-format that can be transformed into surface data by generally available software applications known to those skilled in the art, and vice versa.

Figure 29:
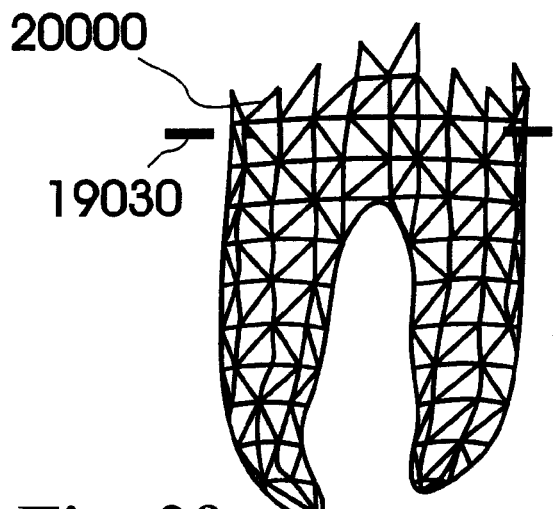
FIG. 29 shows 3D data resulting from the imaging of the root of a natural tooth.
Figure 30:
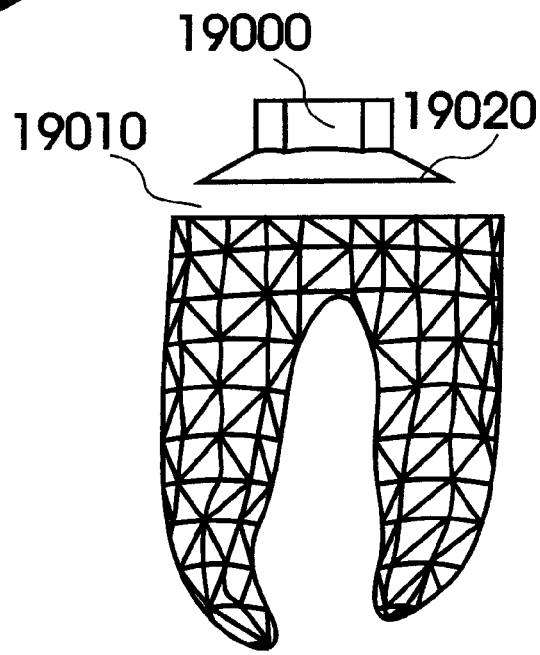
FIG. 30 shows the 3D data of FIG. 29, but cleanly cut at the top, and a virtual hexagon socket from an electronic library.

The scan of the root is then loaded into a CAD software application called MAGICS (Materialise, Leuven, Belgium). Using the cutting features of MAGICS, the occlusal facing edge of the virtual root model (FIG. 29, 20000), which will be uneven and "frayed" in the original scan data, will be straightened in order to receive a clean contour. A straight cut will be performed at a location (19030) where scan data is substantially complete. This is demonstrated in FIGS. 29 and 30. Then, from an electronic library, a virtual hexagon socket is selected and additionally loaded into MAGICS and placed on top of the virtual root, as shown in FIG. 30 (when terms like "top" and "bottom" are used in this context, it is always assumed the root tip points downwards). The hexagon socket consists of the hexagon shape (19000) fitting to the off-the-shelf abutment that will later be mounted to the artificial root, and a junction portion (19020) providing the transition to the virtual root. Since there is a significant variation in root thicknesses and shapes, a selection of hexagon sockets is available in the electronic library, each having a different junction portion in order to receive a minimal gap between the virtual root and the virtual socket.

In a next step, the so-called "stitching" functionality of MAGICS is used to close the gap (19010) between the virtual root and the virtual socket and, if applicable, also other gaps that may be a result of incomplete scanning. The outcome of this step is a virtual representation of a solid. In this context, a three-dimensional solid is an unambiguous numerical description of the surface of the geometrical shape of a three-dimensional object, the numerical description showing no holes and clearly identifying the inside and the outside of the surface.

Figure 31:
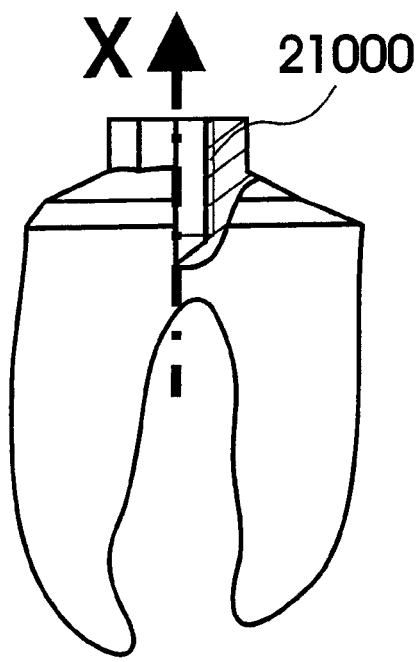
FIG. 31 shows a partial cross-section of an implant having a hexagon socket and a thread for attaching the abutment.

The hexagon socket of the actual prosthesis also needs to have an inside thread (FIG. 31, 21000) to receive the screw used for mounting the crown. In the embodiment, this thread is not part of the virtual model. Rather, the first step of manufacturing is to cut this thread into the workpiece used for fabricating the prosthesis, and then to use it to mount the workpiece to the machine table of the milling machine. To ensure spatial integrity, the coordinate system of the virtual solid must be placed properly. Preferably, the origin of the coordinate system will be placed in the center of the hexagon, one of the main axes running parallel to the midline of the thread as shown in FIG. 31.

The STL data describing the solid representing the tooth are then converted to an IGES data format. This is performed using, for example, a software named SolidWorks (SolidWorks Corp., Concord, Mass., USA). The IGES file allows generating a CNC sequence to machine an artificial tooth from a piece of biocompatible material like titanium or a titanium alloy, that consists for example of more than 60% of titanium. FIG. 33 shows an arbitrary example of a portion of such a file. Ceramic material and other biocompatible materials (including but not limited to stainless steel, synthetics, plastics, resin-modified glass-ionomer cement, hybrid-ionomer cement, resin-enforced cement, and other synthetic and plastic materials) are also applicable. For manufacturing the prosthesis for the above mentioned lower left incisor a workpiece having a size of 20 mm×10 mm×10 mm is adequate. For machining, a traditional 5-axis CNC milling device with a high-speed spindle is used. Other workpiece sizes and multi-axes CNC machining devices can be employed in this context by those skilled in the art.

After cutting the thread that will be located in the center of the hexagon of the finished prosthesis, the workpiece is screwed to an adapter on the machine table of the milling machine by using said thread. The adapter is either shaped so that it leaves sufficient clearance for the milling spindle and the cutter, or a disposable adapter is used so that portions of the adapter itself may be milled off. After teaching the machine the position and inclination of the workpiece, entering the machine and process parameters and overlapping the physical workpiece with the virtual shape, the root shape of the left lower incisor is machined by grinding the workpiece down layer by layer to the desired shape.

After manually cleaning, removing the excess if applicable, polishing, degreasing, etching rinsing, disinfecting and drying the workpiece, it is ready for insertion. In order to improve the integration of the implant into the bone, further treatments according to prior art are possible. Sand-blasting with ceramic particles for instance creates a rough and thus significantly enlarged surface. Coating the surface with hydroxylapatite stimulates bone formation promoting a physico-chemical bond. Other coatings suitable to facilitate include but are not limited to pharmaceuticals, ancestral cells, and proteins. Instead of coating, the aforementioned substances can be applied by others means including but not limited to adjunction and injection.

Before inserting the prosthesis, the extraction socket will be properly cleaned. In a embodiment, the socket will then be filled with Bioplant (Kerr Corporation, Orange, Calif.). Bioplant is a bone promoting substance. It is hydrated with marrow blood from the extraction socket and then injected into the socket using a special syringe delivered with Bioplant. Bioplant fills any voids present between the socket and the implant. After insertion of the implant, additional Bioplant may be applied in order to fully embed the implant below the hexagon socket. FIG. 34 shows the prosthesis embedded in the extraction socket, the voids being filled with Bioplant (13000). In order to avoid the growth of the gum into the void between the implant and the extraction socket, membrane techniques known to those skilled in the art can be employed. Also, the top of the implant excluding the hexagon has been covered with Bioplant. A healing cap is placed on top of the implant. The implant is then secured to the adjacent teeth for about six weeks by means of a light-curing resin strip known to those skilled in the art.

After the implant is healed in, standard procedures of prior art are performed. After an alginate impression has been taken, a customized tray is fabricated, reinforced and perforated where the implant is located. An impression post is screwed onto the implant, and the customized tray is placed onto the dentition. The void between the perforation in the tray and the impression post is filled with impression putty. After the putty has set, the screw attaching the impression pin to the implant is unscrewed, and the impression is removed from the patient's dentition and sent to a specialized laboratory. Based on the impression and an impression of the opposing jaw, the technician will fabricate a crown. When the crown is delivered, the abutment is screwed to the implant, and the crown is cemented onto the abutment.

Another substance suitable to promote bone regeneration is CERASORB DENTAL (curasan AG, Kleinostheim, Germany). It consists mainly of pure phase beta-tricalcium phosphate (beta-TCP). CERASORB is completely resorbed and replaced by natural bone structure. Collagen fibers and blood vessels invade the interconnecting micro-pores of the CERASORB granules (micro-pores) and the inter-granular cavities (macro-pores). The primary-grain size of 10-63 μm does not provoke phagocytosis by macrophages.

Patent Application publication number 2005/0084513, which is hereby incorporated by reference in its entirety, discloses a coating for an implant surface. The coating promotes characteristics on the implant surface such as reducing protein unfolding, preventing inflammatory and fibrotic cell accumulation, reducing the number of such cell attachment sites and preventing other adverse biological reactions. The coating may be applied on any material via physical and/or chemical binding. It may also be used for in vitro purposes.

Another option is to apply nano-crystalline diamond coating. A coating named r-BeSt (Hartstoffbeschichtungs GmbH, Innsbruck, Austria) shows 100% biocompatibility due to the pureness of the diamond coating, an optimal interconnection between substrate and diamond coatings, good tribological properties due to the smoothness of the layer and an active surface for bio-chemical reactions.

Figure 4:
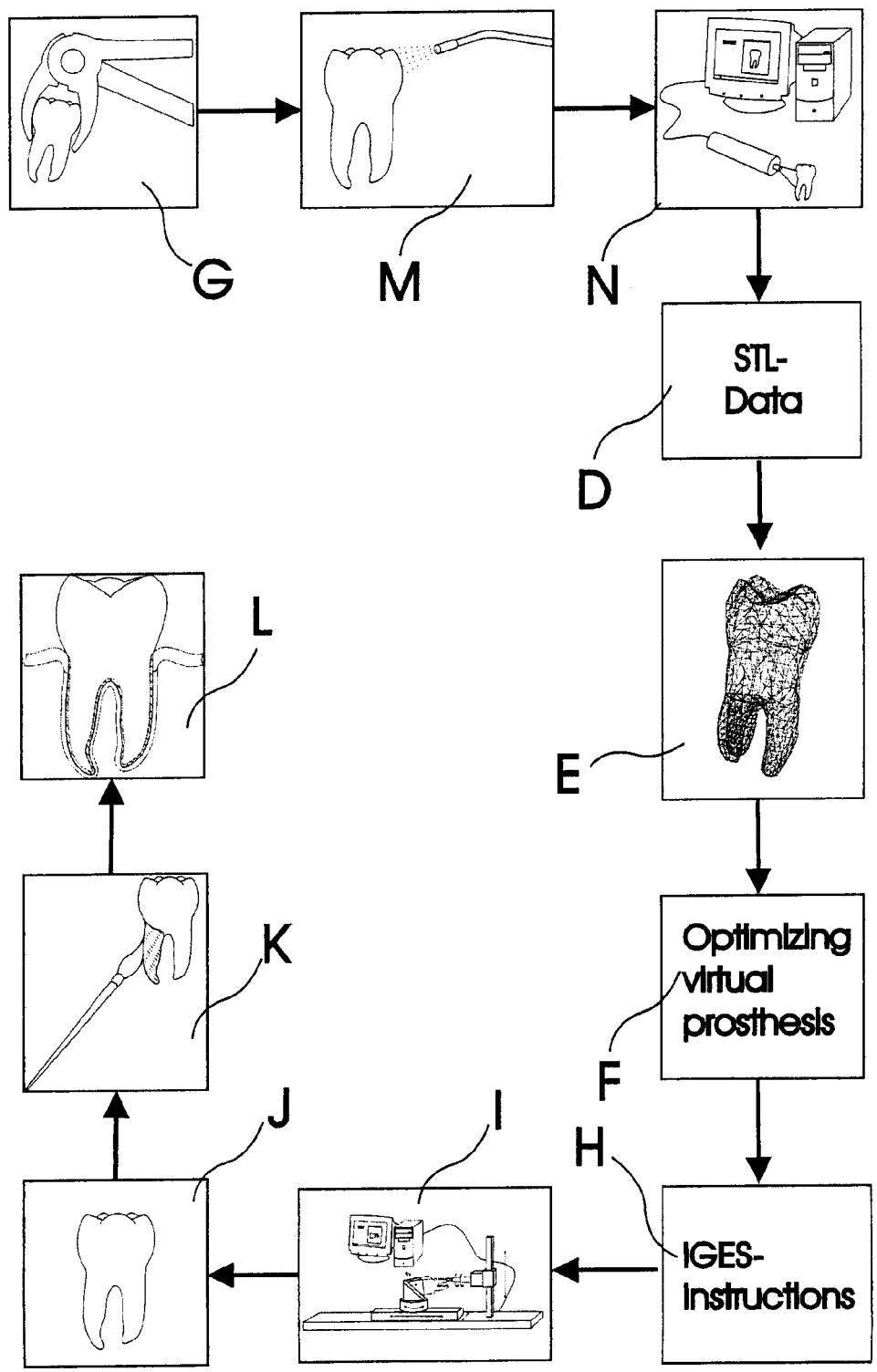
FIG. 4 shows the process steps of extracting the natural tooth, extra-orally acquiring three-dimensional data of that tooth, fabricating an artificial copy and inserting the copy into the socket of the natural tooth according to an embodiment of the invention.

In another embodiment of the invention, an unsegmented prosthesis will be fabricated as shown in FIG. 9. The steps of the process are outlined in FIG. 4. The tooth to be replaced is extracted (step G) and properly cleaned (step M). Then 3D imaging (step N) is performed in order to obtain 3D data representing the three-dimensional shape of the complete tooth. The resulting 3D data (D) is imported into CAD software and displayed to the operator (step E). The shape is modified and optimized as needed (step F, see also FIGS. 23 and 24). The resulting 3D data is converted into IGES format and exported (step H) to a CAM system for fabrication of the prosthesis (step I). The finished prosthesis (J) may be coated with a substance promoting bone ingrowth (step K) and is then implanted into the extraction socket (step L). It should be noted that FIG. 4 contemplates possibly interaction with an operator, one skilled in the art would readily appreciate that this functionality may be fully automated.

The prosthesis is preferably made from a material supporting osseointegration, such as porous calcium phosphate ceramic. This material provides a scaffold for bony ingrowth. In order to fabricate a complete prosthesis, the shape of the crown must also be available. Therefore, after the imaging of the root portion has been completed as described above with respect to FIG. 5, the crown is scanned. It will also be covered with $TiO_2$ powder. A portion of the root of the tooth is attached to the turntable of the scanner while the crown is optically exposed in order to be scanned in the same incremental manner. A second comprehensive STL file is accordingly generated describing the surface of the crown of the tooth. The scan of the root as well as the scan of the crown is performed in a way that a significant overlapping area of the surface of the counterpart is included in each scan.

The scan of the root and of the crown are then loaded into MAGICS and manually maneuvered to a best fit using the overlapping areas of both scans, and merged into one STL data file. In order to increase accuracy, software detecting best fit for two independent surfaces can also be used. After—if required—manually removing outliers of the scanned measurement data and identifying and correcting deficient triangles and adding missing parts, the resulting STL surface data forms a three-dimensional solid representing the overall shape of the extracted tooth.

The STL data is then converted to an IGES data format. For fabricating the above mentioned lower left incisor, a piece of calcium phosphate ceramic having a size of approx. 25 mm×10 mm×10 mm using a traditional 5-axis CNC milling device with a high-speed spindle (about 60.000 rpm), a spherical diamond cutter having a diameter of the tip f the cutter of 1 mm and water cooling. The ceramic workpiece is clamped to the machine table of the milling machine. After teaching the machine the position and inclination of the workpiece, dialing in the machine and process parameter and overlapping the physical workpiece with the virtual shape a first portion representing the root shape of the lower left incisor is machined by grinding down layer by layer the workpiece to the shape of interest. Then a fixture is made for that specific workpiece to clamp the workpiece at the already machined first portion, for instance by grinding a portion of the geometrical negative shape of the fist portion into the receiving part of the fixture.

After teaching the machine position and inclination of the reoriented workpiece clamped into that customized fixture, entering machine and process parameters and overlapping the physical second part of the workpiece with the virtual shape of the second portion to be machined, the crown shape of the left lower incisor is machined by grinding the workpiece down layer by layer to the desired shape. After properly cleaning, removing the excess and degreasing, the prosthesis is ready for insertion into the extraction socket. After the implantation, the artificial tooth is fixed substantially to the same position and inclination of the extracted tooth by being bonded with light curing resin strip to the adjacent teeth.

Figure 17:
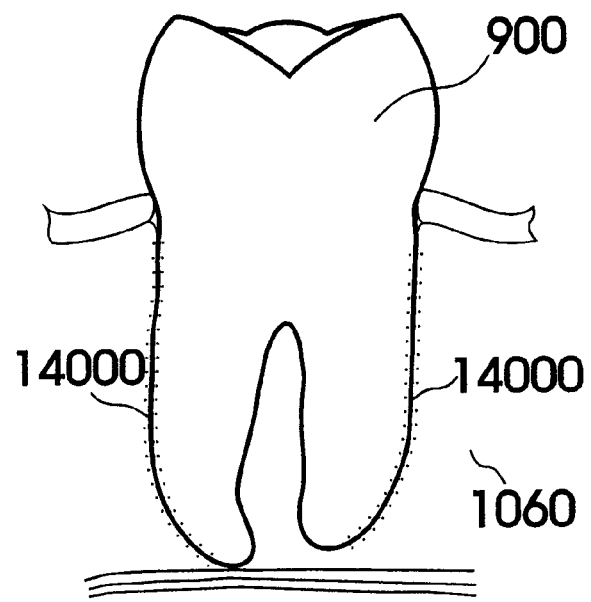
FIG. 17 shows an artificial tooth inserted into the extraction socket and firmly pressed against the walls of the socket in order to promote osseointegration into the bone.

The advantage of this embodiment of the invention is that the complete replacement of the natural tooth is performed in one appointment. After the prosthesis has healed in, only the resin strip initially securing the prosthesis to the adjacent teeth must be removed. A significant amount of laborious steps can thus be avoided. FIG. 17 shows an osseointegrated unsegmented tooth (900). Osseointegration is achieved in marked areas (14000).

Using computer networks, all process steps may be carried out by different and independent parties. The imaging part can for instance be performed at the dentist's office, at a hospital or at a location specialized in imaging. The imaging data can then be transferred to a location where the imaging data are further processed in order to ready them for manufacturing. After the design is finished, the data can again be transferred to the dentist for further optimization and/or approval. Consulting a remote specialist in difficult cases using data transfer may also be applicable. Such a remote specialist may be a clinician or an expert in manufacturing or laboratory procedures. Then, the data can be transferred to a remote manufacturing location. All these data transfers can for instance be performed via the Internet, using preferably Virtual Private Network channels to secure privacy, or through a local area network.

In yet another embodiment shown in FIG. 7, the implant will be made by one type of biocompatible material (9020), for instance, titanium or a titanium alloy, and the portion representing the crown will be coated with another biocompatible material (9010), for instance, ceramic to support both optimal physical strength and esthetics. Alternatively, the crown portion is not coated, but is made from a material different from the material used for the root portion. FIG. 8 shows an artificial tooth, the portion representing the crown being made from a material having optimized esthetic and/or mechanical properties, while the portion representing the root is made from a material promoting periodontal integration. Both portions can be attached to each other by a variety of connection methods: They can be bonded, cemented, fixed mechanically (either by a screw or an interlocking surface), or they can be fabricated from a workpiece that is already comprising different materials. Sintering would be one of the suitable processes. Therefore, the prosthesis can be fabricated either segmented, with the parts being connected to each other either before or after implantation or the complete prosthesis is made in a single process. In another embodiment, a material promoting cell growth and providing good adhesion for cells is used for the root portions. FullCure 720 may serve as an example of such a material. This is an acrylic based photopolymer and distributed by Object Geometries Ltd., Hebron, Israel. This material can be processed by a Rapid Prototyping process named "objet Print". Devices for this process are also distributed by Object Geometries Ltd.

In yet another embodiment, the prosthesis will not be osseointegrated, but adopted by the ligament of the extraction socket. In this case the prosthesis is coated with a material promoting periodontal adoption. A thin layer of about 0.05 mm to 0.2 mm of resin-modified glass-ionomer cement (FIG. 9, 9000) is applied to the surface of the part of the workpiece being inserted into the extraction socket. FIG. 6 shows a segmented artificial tooth, the crown (10000) being made from a material having optimized esthetic and/or mechanical properties, and the root portion (10010) being coated with a substance (9000) promoting periodontal integration, for instance glass ionomer cement. FIG. 9 shows an artificial tooth (9030) made from a material suitable for crowns like ceramics, the root portion being coated with a substance promoting periodontal integration. Substances promoting periodontal integration include but are not limited to pharmaceuticals, ancestral cells, proteins, and cell parts of a human tooth.

Glass ionomer cement is composed of a calcium-aluminosilicate glass powder and an aqueous solution of an acrylic acid homo- or co-polymer. It is a biocompatible material widely used for tooth restorations and provides good adhesion to the ligament. Resin-modified glass ionomer cement can be light-cured. The light activates a catalyst in the cement that causes it to cure in seconds.

After curing, the artificial tooth is implanted and integrated into the existing periodontal tissue formation of that lower left incisor of the patient and fixed substantially into the same position and inclination of the extracted tooth by being bonded with light curing resin strips to the adjacent teeth.

Another option is coating the portion to be implanted with Ca(OH)2-cement. This is a well known substance in dentistry also used to fill root canals. After setting, EMDOGAIN (Institut Straumann AG, Basel, Switzerland) will be applied, a substance containing the enamel matrix protein Amelogenin. EMDOGAIN is resorbed naturally during the normal healing process, leaving only a residue of enamel matrix protein on the coated surface. This natural and insoluble surface layer encourages the population of cementum-forming cells from the surrounding tissues. The newly created surface also functions as an interface between the tooth and the surrounding tissues, preventing down-growth of the epithelial tissues. Again, instead of coating, all the aforementioned substances can be applied by others means including but not limited to adjunction and injection. It may be advisable to prescribe antibiotic pharmaceuticals to reduce the infection risk during the healing process.

Especially in the context of periodontal integration it might be advisable to utilize an absorbable collagen membrane to separate the faster gum growth from the healing process of the periodontal ligament.

In another embodiment an undersized customized root representation of a ceramic prosthesis is coated with a thin layer of mineral trioxide aggregate (ProRoot MTA, Dentsply) while potential socket irregularities are prepared with calcium sulphate (Capset, Lifecore Biomedical) in order to promote the selective formation of new periodontal tissue (i.e., cementum, periodontal ligament, Sharpey's fibers amd alveolar bone) and to build a barrier against an overgrowth by gingival tissue. The thickness of the coating layer should match the undersizing of the root shape and would preferably be chosen to be about 0.2 to 0.3 mm. It would furthermore be advantageous to insert the prosthesis into the socket as soon as possible but no more than 24 hours (see respective reference re: Spouge, Oral Pathology, Mosby, Saint Louis, 1973 above) after extraction.

Periodontal integration (FIG. 10) has the advantage that the anchoring of the prosthesis (200) is not stiff as with osseointegrated implants, but shows the elasticity of the natural tooth. The ligaments (1040) are providing support to the teeth in a viscoelastic manner. Furthermore, forces applied to the tooth and thus to the ligaments create tension which is actually the stimulus for bone growth. Another function of the periodontal ligaments is to serve as a method for sensation. To support periodontal integration, the implantation of the prostheses should be performed shortly after extraction of the natural tooth, preferably not more than 24 hours after extraction. The key to success is the preservation of cellular vitality in the periodontal ligament and performing the extraction in a surgical environment under conditions of asepsis. Further below, other embodiments of the invention are disclosed providing instant replacement of the natural tooth.

In another embodiment, suitable pre-determined generic root shapes can be selected and employed fabricating the portion of the implant to be osseointegrated or integrated into the periodontal ligament. A variety of generic shapes may be stored on a computer-readable media and accessed by the CAD/CAM system.

Another product that is helpful in adapting an implant into the extraction socket is Atrisorb (CollaGenex Pharmaceuticals, Inc., Newtown, Pa.). It helps regrow healthy bone and soft tissues and forms a barrier creating a space in which tissue can grow. Atrisorb is applied as gel and forms a barrier membrane when sprayed with sterile water. It maintains structural integrity for approximately six months. Complete bioabsorption is achieved within nine to twelve months.

In order to assure that only the desired portions of the prosthesis are adopted by the periodontal tissue, other portions, like the surface intended to carry the crown later to be attached to the implant, may be covered with a substance preventing such adoption. Silver is for instance a biocompatible material suitable for that purpose. The Fraunhofer Institute for Manufacturing Technology and Applied Materials Research (IFAM) has developed a nanocomposite plasma coating technology that can be used for applying a thin layer containing silver.

In yet another embodiment, the crown of the extracted tooth or the tooth to be extracted is not only subject to 3D imaging, but additional color data are obtained. Depending on the scanning method, color data can already be contained in the scan data, or a separate imaging is performed to record the color of the crown. It is possible to obtain a uniform overall color representing the average color of the crown, or alternatively different shadings for different portions of the crown can be recorded. Basing on the color data, the color of the crown can be adapted to the color of the original tooth. The lab technician manufacturing an artificial crown can for instance be provided with the color data and select the most appropriate color for the prosthesis. If a complete prosthesis is manufactured using CAM methods, a material best fitting the original color can be used, or a coating can be selected that matches the original color.

In another embodiment, no fixture is used to manufacture the second portion of the artificial tooth. Instead, dedicated features elements will be added to the shape of the root, such as small holes or posts sticking out, allowing for precise positioning of the artificial tooth for the second step, which is manufacturing the crown portion. These dedicated features will be removed or closed after the complete tooth has been fabricated.

In yet another embodiment, a Rapid Prototyping process is used for fabricating a prosthesis from hybrid materials. The Rapid Prototyping process may build the prosthesis layer-by-layer. For instance, a powdery layer of a substance can be applied on top a workpiece, and then portions of the new layer are hardened by a controlled laser beam, while the other unhardened portions are later be removed. In this manner, different substances having different properties (stiffness, hardness, biological properties etc.) can be applied and therefore different portions of the workpiece be made from different materials. In one embodiment, the crown is made from a material different from the one used for the crown. In yet another embodiment, the portions representing dentine are made from a material different from the one used for the portions representing enamel.

In another embodiment, the three-dimensional data used to fabricate the dental prosthesis is not acquired from an extracted tooth, but obtained intra-orally, the tooth to be replaced still in place. The advantage of this embodiment is that the complete digital preparation and also the manufacturing steps of the artificial replacement can be performed prior to the extraction. Only when the artificial tooth or segment to be implanted is ready for insertion, the original tooth is extracted. Immediately after extraction, the artificial tooth can be implanted. This contributes to a better healing of the trauma.

Figure 3:
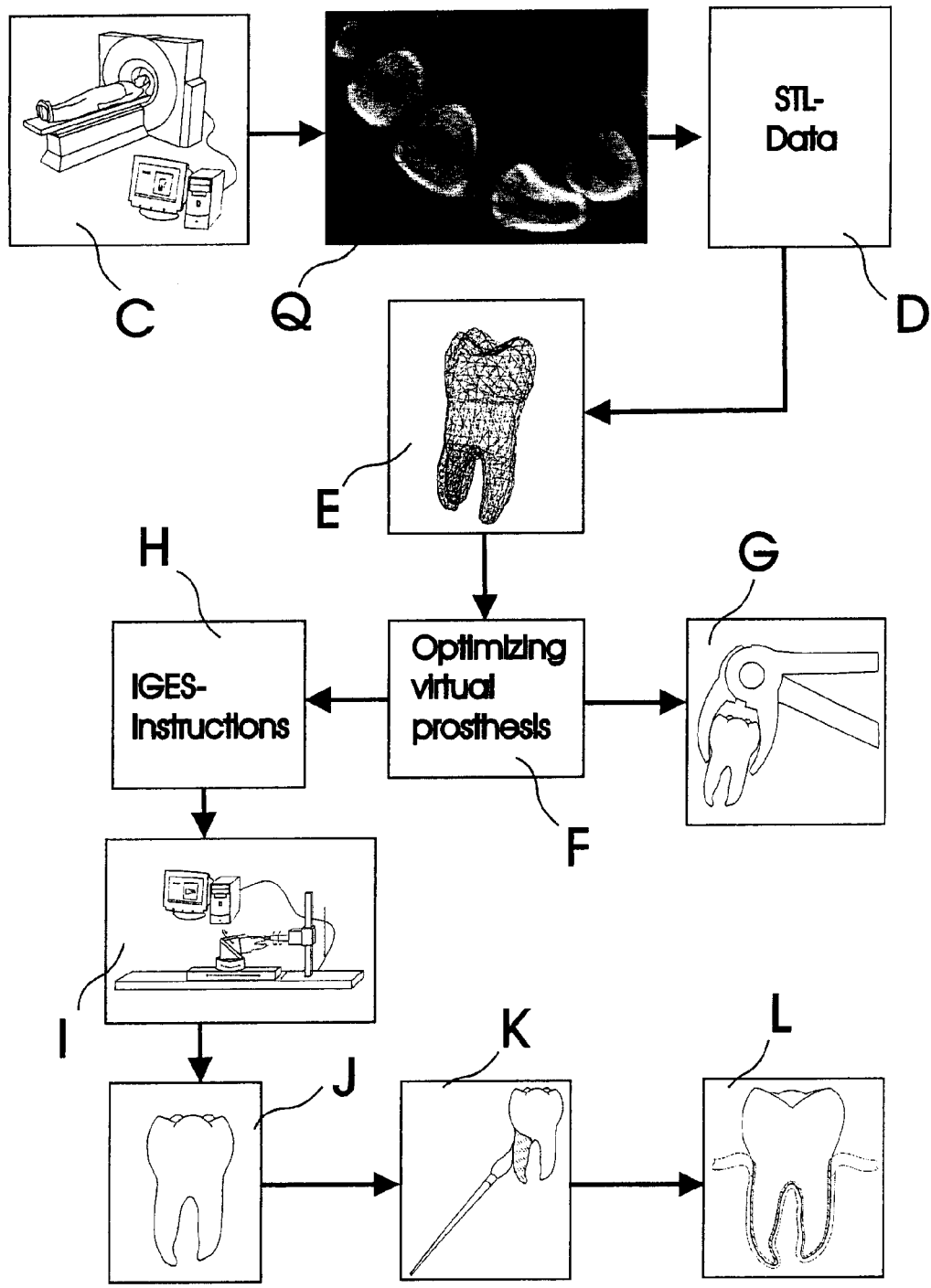
FIG. 3 shows the process steps of intra-orally acquiring three-dimensional data of a human tooth, fabricating an artificial copy, extracting the natural tooth and replacing it with the artificial copy according to an embodiment of the invention.

FIG. 3 outlines the process steps. A CT scan (steps C, Q) is made of the dentition of the patient. The resulting 3D data (D) is imported into CAD software and displayed to the operator (step E). The shape is modified and optimized as needed (step F). The resulting 3D data is converted into IGES format and exported (step H) to a CAM system for fabricating the prosthesis (step I). The process may include coating the finished prosthesis (step J) with a substance promoting bone ingrowth (step K). Only after the prosthesis is ready for insertion, is the natural tooth extracted (step G), and the implant is placed into the extraction socket (step L). It should be noted that FIG. 3 contemplates possibly interaction with an operator, one skilled in the art would readily appreciate that this functionality may be fully automated.

A NewTom 3G-MF12 Cone Beam CT (NewTom Deutschland AG, Marburg, Germany) will preferably be used to acquire the imaging data. The accuracy of the measurement data will be better than 0.2 mm and therefore highly sufficient for the process. A spline CT with a small envelope dedicated to dentistry like the Morita can deliver 3D data with even better resolution.

Further methods for intra-oral imaging include but are not limited to CT, CBCT, MRT, ultra sound, active triangulation, passive triangulation, confocal scanning, and TOF (Time Of Flight). The anatomical structures obtained by intra-oral imaging include but are not limited to periodontal structure, the alveolus, and the jaw bone of the patient.

Using intra-oral 3D imaging, it is even possible to perform a scan of a patient long in advance and to file the personal imaging data of the dentition of the patient. In case of an injury or accident where teeth get lost or busted or are not available for a scan for any other reason, a fabrication of individual prostheses can be initiated immediately, using the previously collected imaging data.

Figures 13, 14:
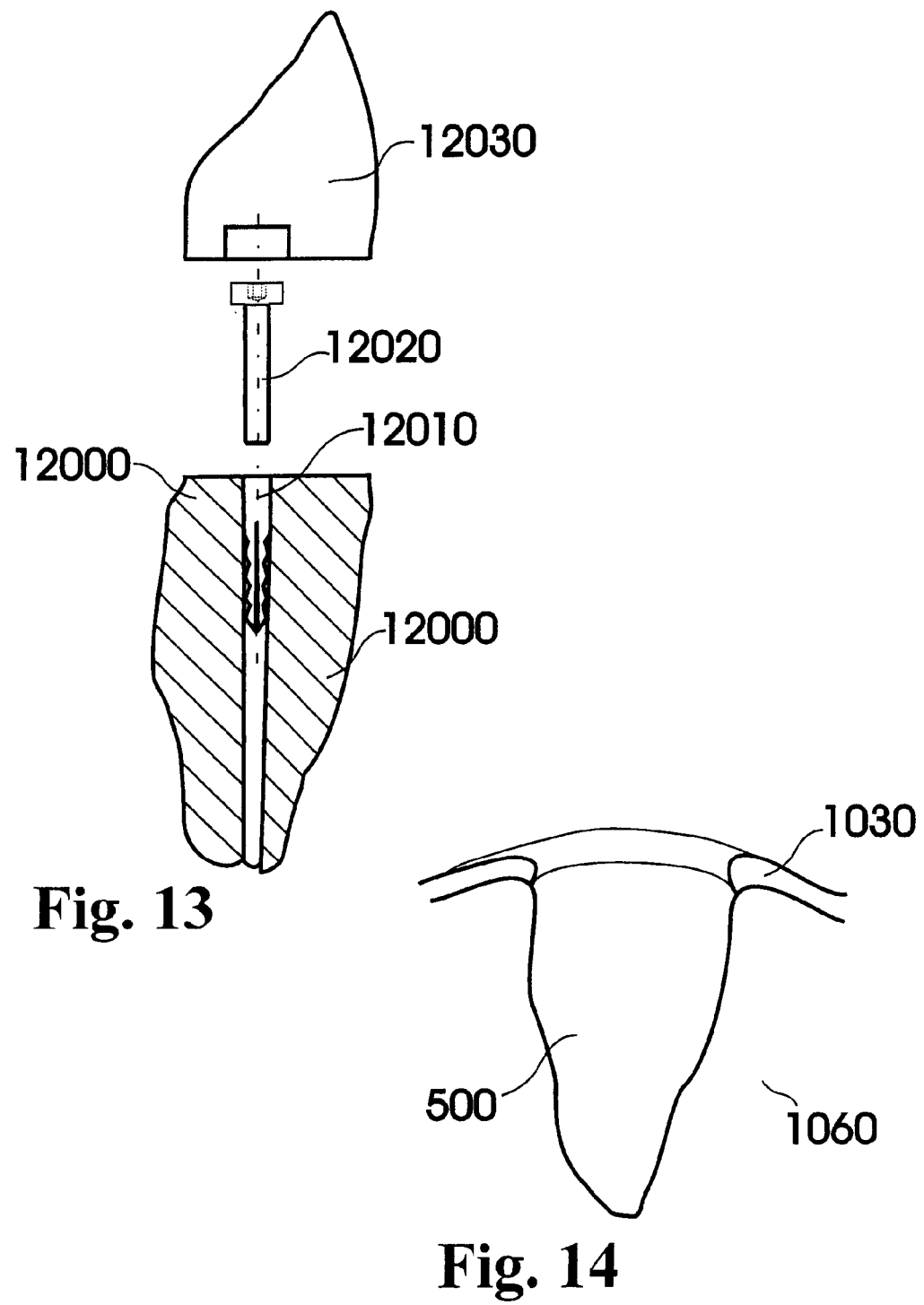
FIG. 13 is a cross-sectional view of a segmented artificial tooth, the segment representing the root being expanded using a screw and a dowel in order to support osseointegration and improve physical stability after implantation.
FIG. 14 shows an extraction socket.

Instead of 3D imaging and digitally processing imaging data, copy milling or copy grinding from the original tooth or parts or the tooth can be performed. The root can also be shaped according to an impression made directly from the alveolus of the extracted teeth as shown in FIG. 14, using a specialized material or using standard impression materials separated from the surface (periodontal ligament or bone) of the alveolus (500) by a very thin film of plastic or another material suitable for the purpose. Alternatively an impression can be taken from the extracted tooth. Laboratory methods for fabricating dental prostheses basing on impressions are readily available. These methods are mostly using casting processes or employing light curing or chemical curing processes where monomer components are polymerized to molecular networks. Further methods of fabricating a substantial copy of the original tooth include but are not limited to depositing, sintering, 3D printing, molding, curing, grinding and milling. The ongoing progresses made in rapid prototyping, that is fabricating individual parts directly basing on digital data, will strongly contribute to this invention.

Figure 23:
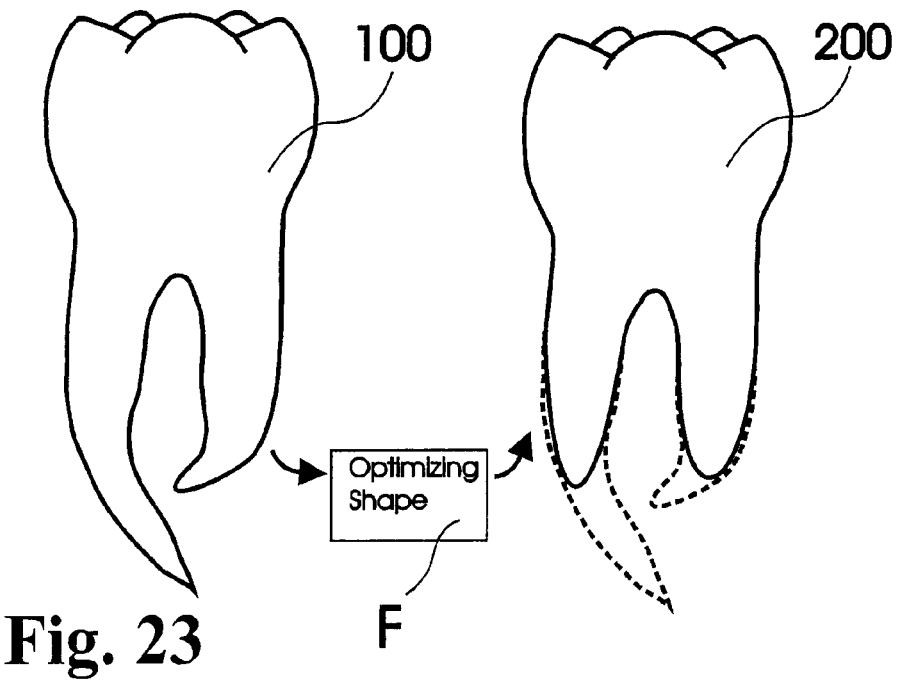
FIG. 23 shows a natural tooth having strongly crooked roots and the artificial substitute, wherein the shape of the substitute has been altered in order to allow for simplified insertion into the natural socket.
Figure 24:
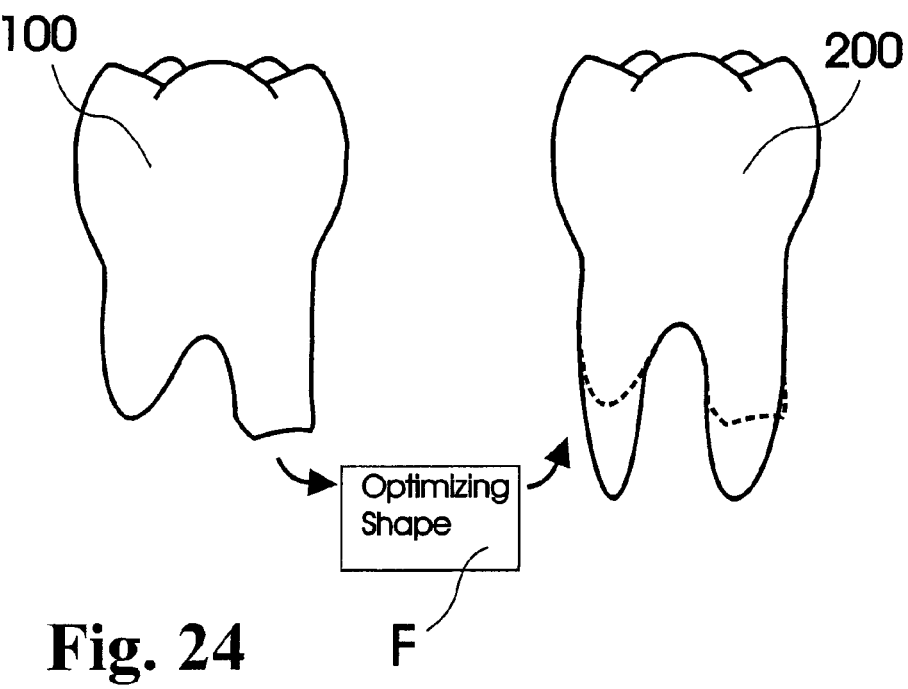
FIG. 24 shows a natural tooth suffering from partial root loss due to root resorption or a surgical procedure and an artificial substitute, the shape of the artificial tooth being optimized for better adaption to the natural socket.
Figure 25:
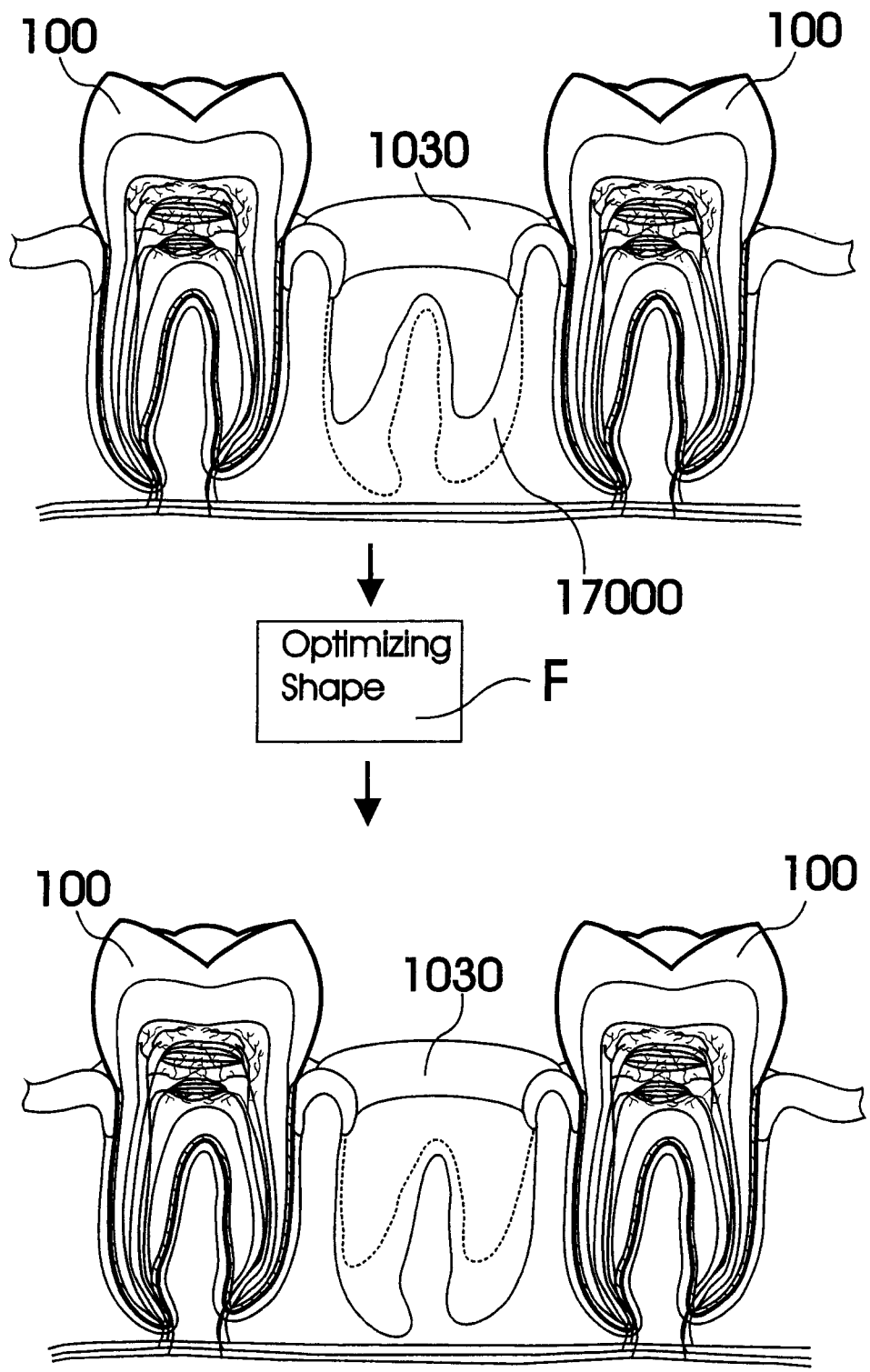
FIG. 25 shows a tooth socket after extraction. Due to root resorption, the size of the socket has been reduced over time. In order to enhance anchoring, the artificial replacement will have a root portion of greater size. Therefore, the socket is surgically enlarged.

In some cases the shape of the original roots will present difficulties on the insertion of the artificial replacement. In such cases, a proper modification and optimization of the shape of the artificial root according to FIG. 23 is applicable. In other cases, the root of the natural tooth may be suffering from partial root loss due to root resorption or a surgical procedure. In these cases, the root of the replacement may be adapted to the extraction socket as demonstrated in FIG. 24. For example, the customized portion includes a substantial copy of at least 60% of the root shape of the natural tooth while the other portion of the artificial root is modified as described herein. In other cases, the size of the socket may have been reduced over time due to root resorption as displayed in FIG. 25. The size reduction has occurred in areas (17000). In such cases, it is advantageous to enhance anchoring by surgically enlarging the socket and to adapt the root of the artificial tooth to the enlarged socket. SolidWorks is a suitable CAD software to alter the shape of the implant with respect to the original imaging data.

Figure 22:
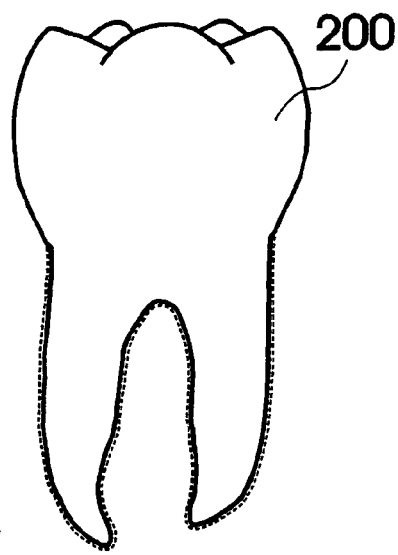
FIG. 22 shows an artificial tooth, the portion representing the root being slightly reduced in size compared to the natural tooth.

There are more reasons to modify the shape of the implant with respect to the original root. To ease insertion into the extraction socket, the shape of the implant may be slightly undersized as shown in FIG. 22. MAGICS provides a functionality allowing for a simple reduction of the overall size of a body. On the contrary, an oversized artificial root may be desirable in order to receive a very tight mechanical fit in the extraction socket to promote osseointegration as displayed in FIG. 17. This can also easily be achieved with MAGICS. This software has a couple of helpful features that have originally been developed to optimize plastic parts for injection molding, but turn out to be useful also for the processes of this invention.

In yet another embodiment of the invention, original portions of the natural tooth will be integrated into the implant. Especially portions of the root still being covered with cementum will greatly improve adoption into the ligaments of the extraction socket. On order to integrate those natural portions, they will be cleaned and prepared for imaging as described further above. The resulting 3D imaging data will be imported into MAGICS and processed like the data of a complete tooth. The three-dimensional virtual body will then be placed at the proper location with respect to the virtual body representing the shape of the implant to be produced. Using boolean functions of MAGICS, the body representing the natural portion(s) of the tooth will be subtracted from the body representing the implant, thus creating a cavity in the implant having the exact size and shape of the natural portion (s) of the tooth to be integrated into the implant. After the implant has been fabricated and processed, the natural portions of the tooth are cemented into the implant.

Figure 15:
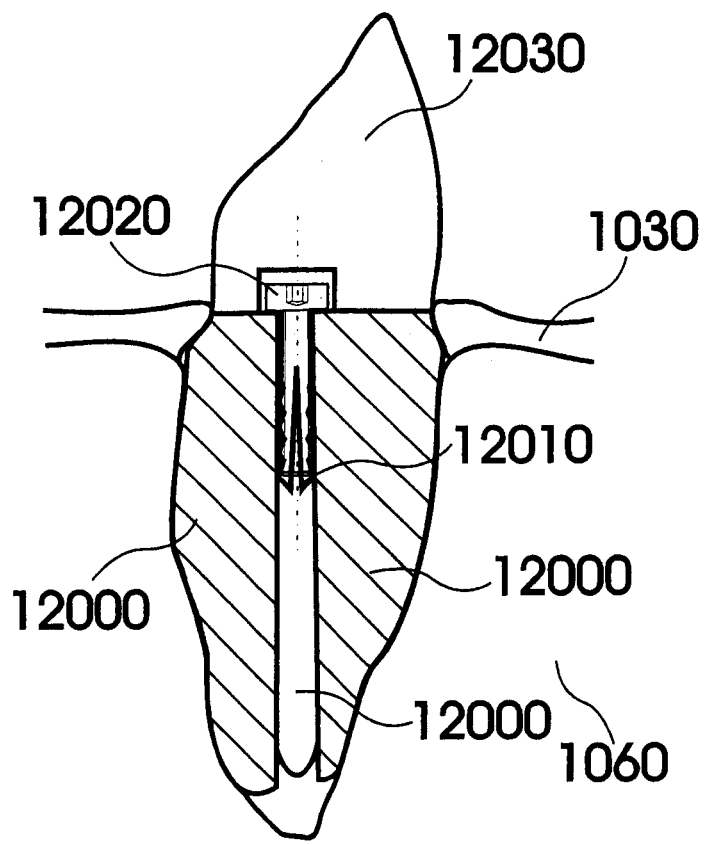
FIG. 15 is the artificial tooth of FIG. 13 inserted into the extraction socket and expanded.
Figure 16:
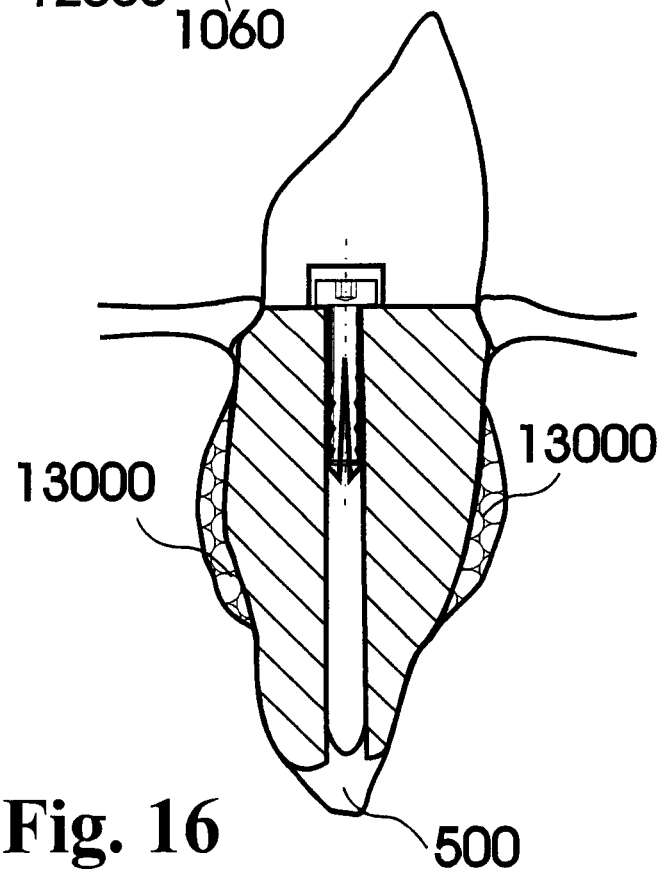
FIG. 16 is a view of an artificial tooth according to FIG. 15, wherein voids between the socket and the tooth are filled with a bone promoting substance.
Figures 35, 36:
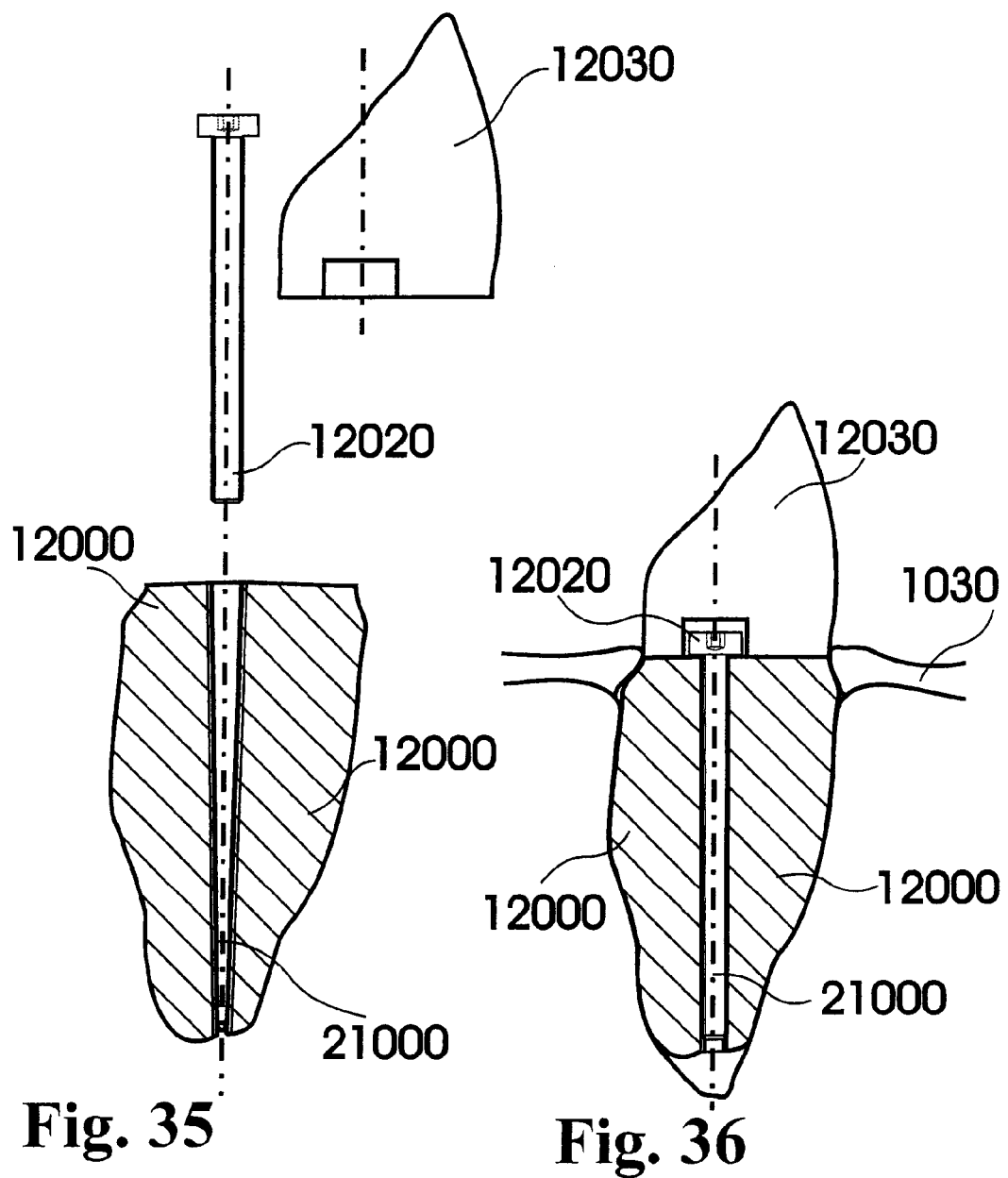
FIG. 35 is a cross-sectional view of the components of a segmented artificial tooth, the segment representing the root being expandable by being slotted and having a conical thread.
FIG. 36 is the artificial tooth of FIG. 35 inserted into the extraction socket and being expanded by inserting screw into the conical thread.

In yet another embodiment of the invention, firm anchoring of the implant is achieved by expanding the portion being located in the extraction socket in order to support osseointegration and improve physical stability after the implantation. By expanding the implanted portion, forces are applied to the alveolus or bone. In this embodiment, the artificial root is shaped to form an expansion anchor. Expansion can be achieved by either using a material changing its shape due to temperature changes after insertion like SMA (shape memory alloy) or by using a material like shape memory polymers activated by electromagnetic radiation. Expansion can also be achieved mechanically by placing a dowel inside the artificial root. This is demonstrated in FIGS. 13 and 15. The root portion of the implant is slotted thus forming posts or wings (12000) and made from a material providing sufficient elasticity in conjunction with the slots. When screw (12020) is inserted into dowel (12010), the posts are pressed against the walls of the extraction socket. The crown (12030) is attached to the implant after insertion, using standard procedures known in prior art. FIG. 16 displays such an implant located in an extraction socket where voids have been filled with a substance (13000) promoting bone growth like Bioplant or CERASORB. In FIG. 35 another embodiment is displayed. No dowel is used, but instead the thread is conical. When screw (12020) is inserted into the conical thread, the wings (12000) are accordingly expanded and pressed firmly against the extraction socket, as demonstrated in FIG. 36. Alternatively the initial pressure supporting the fast integration into the bone may be performed by for example three oversized small grooves positioned on the outer surface parallel to the longitudinal axis of the root causing pressure when the artificial root will be inserted.

To achieve a long living prosthesis the size and the shape of the root and the socket needs to be appropriate to enable solid anchorage in the bone. If for example a root is too small to absorb the normal chewing forces it may be necessary to expand the size of the socket before designing and manufacturing the customized root. Other patients may not have enough bone material, so that the thickness of the bone gingivally and labially is not sufficient for the anchorage of an implant. In such a case, the root may be shaped like a clamp so that the corticalis is used for the anchorage. This approach is known as "juxtaosseous" method (the implant adapts to the bone and not the bone to the implant). If an appropriate material like Titanium in combination with biological ossifying substance is used, the bone adapts to the implant and so the implant becomes an osseointegrated implant. For abutments this is already successfully being used by the San Babila Day Hospital in Italy. Even more solidity can be achieved by a "multi-legged" root shape combining an artificial root and clamp shaped outer part for the adaptation to the corticalis. This approach significantly increases the stability of the anchorage because no hollow or less stabile areas remain in the bone. If crown and root are manufactured as one part, the crown may be coated with an enamel-colored layer for aesthetic reasons. During the healing process appropriate measures need to be put in place to avoid early exposure of the implant to forces (bite bumpers, partials positioners, etc.).

Figure 20:
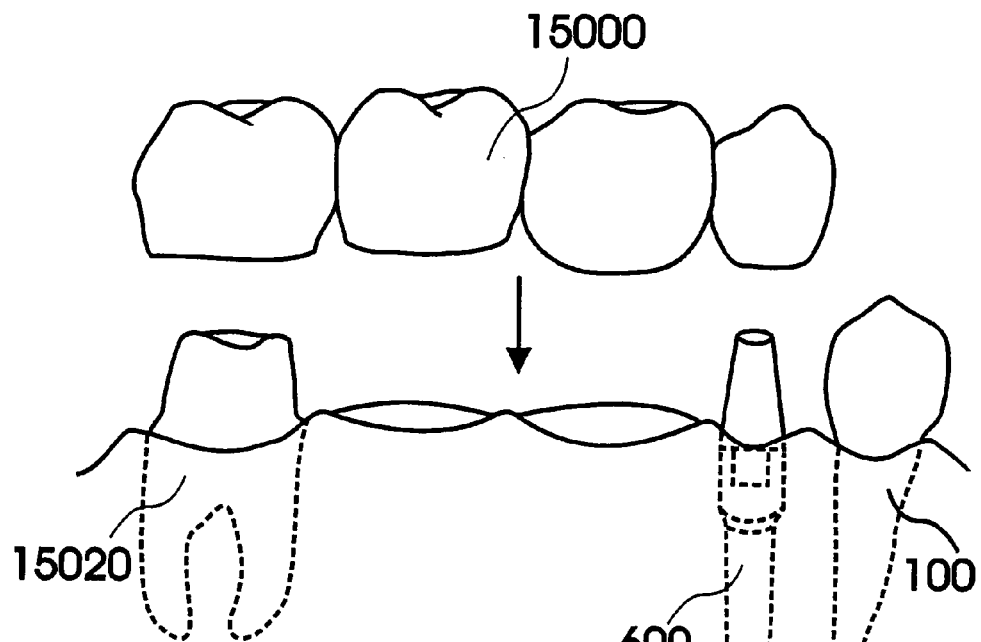
FIG. 20 is a view of a bridge according to prior art.
Figure 21:
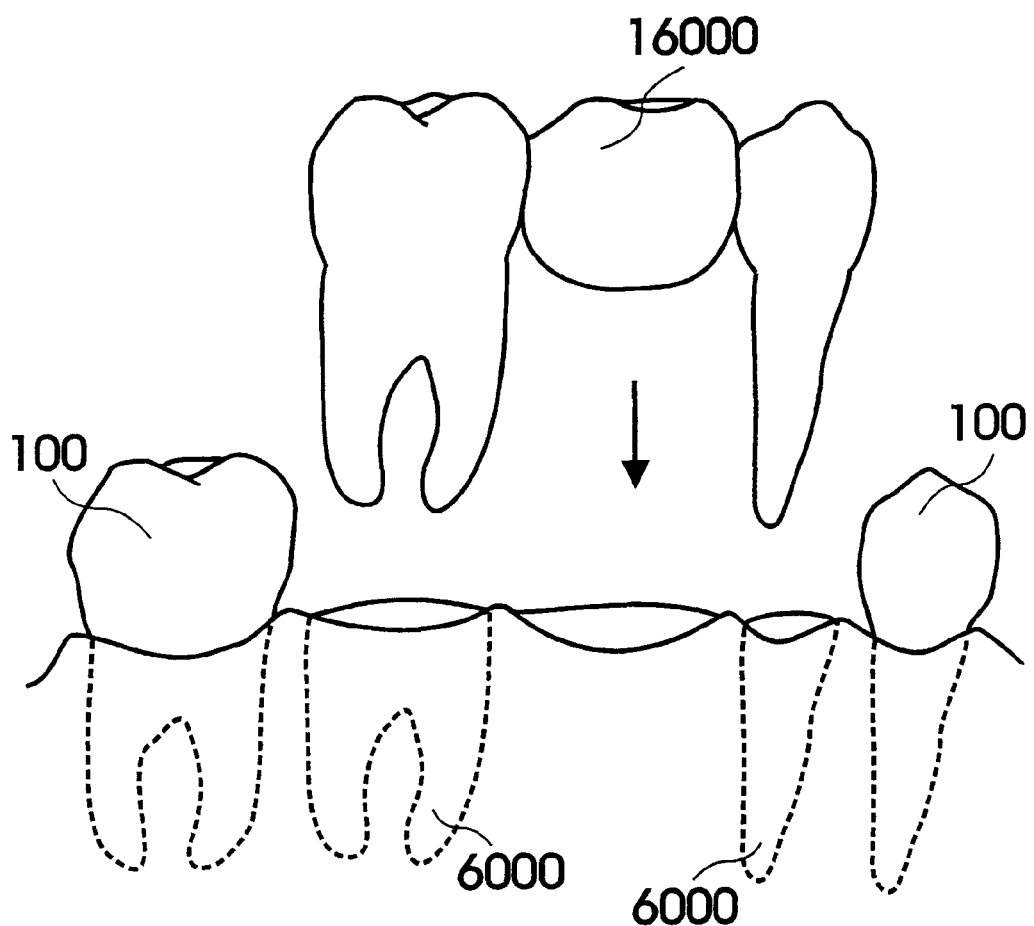
FIG. 21 is a view of a bridge according to an embodiment of the present invention.

The invention is not limited to the replacement of a single tooth. It is possible to manufacture dental bridges, the lateral teeth having root features that can readily be implanted into an existing socket. Conventional dental bridges (15000) as displayed in FIG. 20 are cemented onto natural teeth with the crown being grinded down (15020) or onto conventional implants (600). According to this invention, the natural sockets (6000) will be used as shown in FIG. 21 for attaching the bridge (16000), the adjacent teeth (100) staying healthy and complete. It is also possible to fabricate a partial prosthesis to be implanted into the natural socket, said prosthesis being the anchor for a later installment of a dental bridge. This embodiment is especially useful in cases where one of the two lateral supports of the bridge is already present, and the bridge therefore needs to be cemented.

In all of its embodiments, due to the ability of the suggested manufacturing processes, the invention allows the fabrication of prostheses representing crowns, roots, bridges, segments or any combination thereof, and also the entirety of a dentition.

In another embodiment, off-the-shelf abutments will be integrated into the artificial root using the intended connection method recommended by the manufacturer like screwing them into the artificial root with or without drilling a hole, clicking them onto a counter shape or others.

In yet another embodiment, the components will be molded directly into the artificial root.

In yet another embodiment, the artificial root will comprise a feature on its occlusal-facing surface shaped in a way that it allows for assembly of a conventional veneer or a pre-manufactured veneer or crown to the root. The occlusal-facing surface can also be shaped to provide an interlocking connection to the crown as shown in FIG. 12. The occlusal surface can also have all kinds of connecting features (11000) symbolized in FIG. 11 to allow for attachment of a crown (12050).

Figure 18:
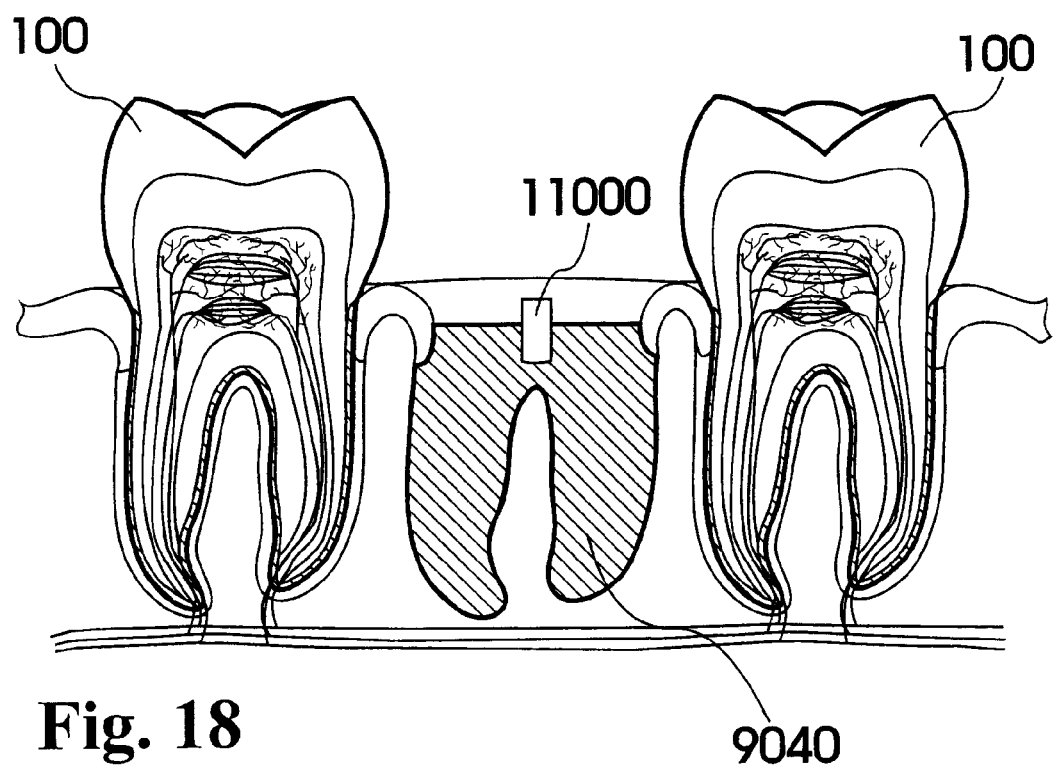
FIG. 18 shows an extraction socket of a patient, the socket filled with a bone promoting substance, and a connection element for the root being embedded into the bone promoting substance.
Figure 19:
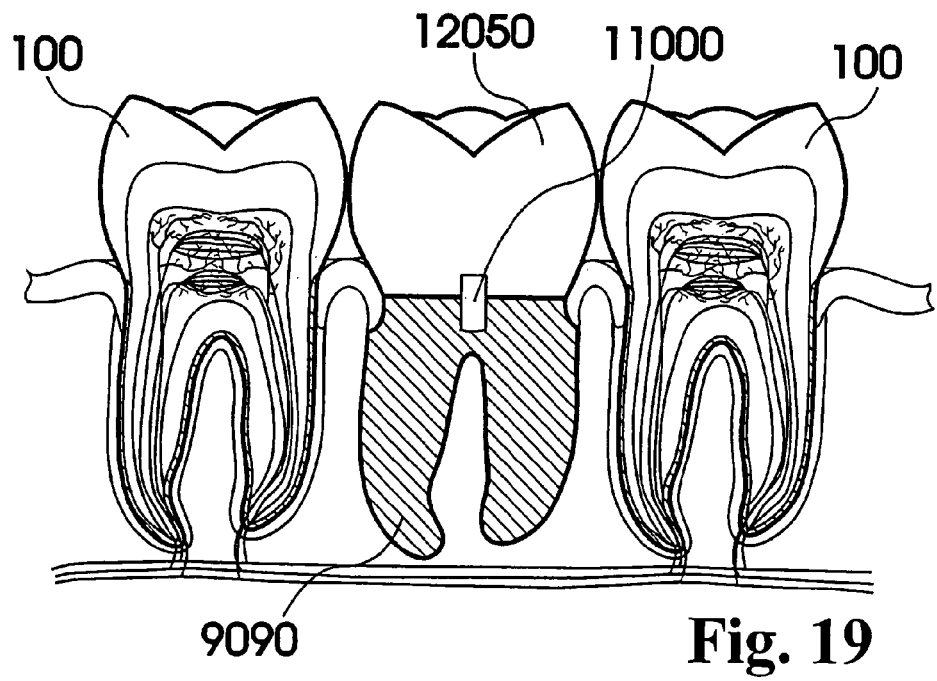
FIG. 19 shows an artificial crown attached to the connection element of FIG. 18 after the bone promoting substance has been replaced by newly grown bone.

In yet another embodiment as shown in FIG. 18 the extraction socket will be filled with a bone promoting substance (9040), and a connection element (11000) for the root is embedded into the bone promoting substance. FIG. 19 shows the artificial crown attached to the connection element of FIG. 18 after the bone promoting substance has been replaced by newly grown bone (9090).

In another embodiment the time needed for the adoption into the periodontal ligament will be reduced and/or the strength and/or the life-time of the connection to the surface of the artificial root will be optimized by increasing the surface by sandblasting, adding a mesh or other suitable means and/or pharmaceutics or other substances supporting the integration of the chosen material of the artificial root into the periodontal ligament like the protein amelogenin. These pharmaceutics will be applied by all conventional or state-of-the-art methods like dry or liquids suspensions to be painted onto the artificial roots before integration, or by injection with a hypodermic needle or intra-orally through pills. Also ancestral cells may be used to support the rebuilding of the periodontal ligament.

Membrane techniques may be used to protect the area dedicated to the relatively slow growing periodontal ligaments from the fast growing gingival epithelium.

In another embodiment decreasing the time needed for the osseointegration and/or to increasing the strength and/or the life-time of the connection to the surface of the artificial root will be achieved by increasing the surface by sandblasting, adding a mesh or other suitable means and/or pharmaceutics supporting the integration of the chosen material of the artificial root into the bone. These pharmaceutics will be applied by all conventional or state-of-the-art methods like dry or liquid suspensions to be painted onto the artificial roots before integration, or by injection with a hypodermic needle or intra-orally through pill and/or ray treatment.

In another embodiment the shape of the artificial root will not completely reflect the shape of the root to be replaced. In order to strengthen the connection with the periodontal ligament or the bone, the shape will be modified. If for instance the three roots of a molar are located very close to each other, the three roots will be replaced by only one root which will comprise parts of the original shape of the three original roots.

There is a lot of software readily available on the market that allows for easy and intuitive modification of 3D shapes. Both previously mentioned programs MAGICS and SolidWorks are suitable for this task.

In another embodiment the closure of remaining gaps between the artificial root and the socket used for implantation will be accelerated by suitable pharmaceutics and/or ray treatment.

It is obvious to anybody skilled in the art that various aspects of the invention as explained above can readily be combined with each other.

The meaning of "CAD" shall include but shall not be limited to any and all technology of computer aided design.

The meaning of "CAM" shall include but shall not be limited to any and all technology of computer aided manufacturing.

The meaning of "CNC" shall include but shall not be limited to any and all technology of computer numerical control as it relates to manufacturing machinery and systems, including but not limited to rapid prototyping devices and systems.

The meaning of "Rapid Prototyping" shall include but shall not be limited to all technologies qualified for manufacturing of copies of virtual three-dimensional objects and also technologies qualified for mass customization or the mass production of copies of customized or adapted geometries to the needs of an individual patient.

The meaning of "body" of an artificial tooth shall include but shall not be limited to the part of the prosthesis representing a root structure for periodontal or osseointegration or the combined part of the prosthesis representing a root structure for periodontal or osseointegration and a support structure for a crown or a bridge.

The meaning of "prosthesis" shall include any substantially artificially shaped part of any natural and artificial material. In this sense a dental prosthesis for periodontal integration would have to be distinguished to any human tooth used for intentional re-implantation.

Whenever the context requires, the word "prosthesis" shall be deemed to include the word "implant" and vice versa.

"3D" shall mean three-dimensional.

The meaning of "CT" shall include but shall not be limited to any and all technology of computed tomography.

"CBCT" shall mean cone beam computed tomography.

The meaning of "MRT" shall include but shall not be limited to any and all technology of magnetic resonance tomography.

The meaning of "TOF" shall include but shall not be limited to any and all technology employing time of flight procedures.

The meaning of "imaging" and "scanning" shall include but shall not be limited to any and all technology of acquiring two-dimensional and/or three-dimensional data of physical objects or parts of a human body.

The meaning of "periodontal ligature" or "periodontal ligament" shall include but shall not be limited to the fibrous connective tissue interface usually located between a human tooth and the anatomical structure of the jaw of a human being.

The meaning of "periodontal integration" shall include but shall not be limited to the integration into the periodontal ligament structure.

In this sense a prostheses for periodontal integration would have to be distinguished to any osseointegrated implant.

The meaning of "cavity" shall include but shall not be limited to the periodontal cavity, a cavity of the jaw bone structure, a cavity of the alveolus or a combination thereof.

The meaning of "extraction socket" shall include prepared or unprepared extraction sockets. The meaning of "prepared" shall include but shall not be limited to being surgically pared or surgically abraded.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The various embodiments and aspects of embodiments of the invention disclosed herein are to be understood not only in the order and context specifically described in this specification, but to include any order and any combination thereof. Whenever the context requires, all words used in the singular number shall be deemed to include the plural and vice versa. Words which import one gender shall be applied to any gender wherever appropriate. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

In the drawings and specification, there have been disclosed embodiments of the invention, and although specific terms are employed, the terms are used in a descriptive sense only and not for purposes of limitation, the scope of the invention being set forth in the following claims. It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the disclosure herein and within the scope of this disclosure patent, which is limited only by the following claims, construed in accordance with the patent law, including the doctrine of equivalents.

In the claims which follow, reference characters used to designate claim steps are provided for convenience of description only, and are not intended to imply any particular order for performing the steps.

What is claimed:

1. A dental prosthesis to be integrated into a jaw bone cavity of a pre-identified patient, the prosthesis being a finished manufactured product prior to its insertion into the jaw bone cavity, the prosthesis comprising:

a root portion configured to be positioned in and integrated into a jaw bone cavity of a specific pre-identified patient and having an outer surface, the outer surface having a custom three-dimensional surface shape specifically dimensionally matching a three-dimensional surface shape of corresponding outer surface portions of a root of a natural tooth of the pre-identified patient removed from the jaw bone cavity of the pre-identified patient, the root portion further comprising a biocompatible enhancement selected from the group comprising:

a cured cement forming substantial portions of the outer surface of the root portion, the cured cement having a composition to enhance integration of the root portion into and adoption by a periodontal ligament cell structure within the jaw bone cavity receiving the root portion and being selected from the group consisting essentially of calcium hydroxide cement, glass-ionomer cement, resin-modified glass-ionomer cement, and light-activated resin-modified glass ionomer cement, and a layer of mineral trioxide aggregate forming substantial portions of the outer surface of the root portion.

2. A dental prosthesis as defined in claim 1, wherein the root portion comprises a root main body portion, the root main body portion comprising one of the following: a ceramic and a biocompatible metal, having portions of the natural tooth integrated therewith.

3. A dental prosthesis as defined in claim 1, wherein the biocompatible enhancement further comprises ancestral cells located on the outer surface of the root portion.

4. A dental prosthesis as defined in claim 1, wherein the biocompatible enhancement further comprises cells of a tooth positioned on the outer surface of the root portion.

5. A dental prosthesis as defined in claim 4, wherein the cells of a tooth are human cells.

6. A dental prosthesis as defined in claim 1, wherein the root portion comprises a root main body portion having a root main body outer surface, the dental prosthesis further comprising:
   a permanent crown portion connected to the root portion of the dental prosthesis to form a unitary prosthetic structure existing as the unitary prosthetic structure; and
   an enamel-colored layer of surface material abuttingly contacting a substantial portion of the outer surface of the permanent crown portion, wherein
   the biocompatible enhancement comprises a biocompatible coating material comprising the cured cement abuttingly contacting a substantial portion of the root main body outer surface of the root main body.

7. A dental prosthesis as defined in claim 1, wherein the biocompatible enhancement comprises the cured cement forming substantial portions of the outer surface of the root portion.

8. A dental prosthesis as defined in claim 7, wherein the cured cement comprises calcium hydroxide cement.

9. A dental prosthesis as defined in claim 7, wherein the cured cement comprises glass-ionomer cement.

10. A dental prosthesis as defined in claim 7, wherein the cured cement comprises the resin-modified glass-ionomer cement, the resin-modified glass-ionomer cement formed of a calcium alumino-silicate glass powder and an aqueous solution of an acrylic acid homo- or co-polymer.

11. A dental prosthesis as defined in claim 7, wherein the cured cement comprises the light-activated resin-modified glass ionomer cement, activated prior to insertion into the root portion of the jaw bone cavity of the pre-identified patient.

12. A dental prosthesis as defined in claim 1, wherein the biocompatible enhancement comprises:
   a first layer of biocompatible material comprising one or more of the following: a layer of between 0.05 mm and 0.2 mm of the resin-modified glass ionomer cement, the glass ionomer cement comprising a calcium-aluminosilicate glass powder and an aqueous solution of an acrylic acid homo- or co-polymer, the layer of mineral trioxide aggregate, the light-activated resin-modified glass ionomer cement, and the calcium hydroxide cement; and
   a second layer of biocompatible material suitable to be integrated into and adopted by the periodontal ligament structure when the dental prosthesis is positioned in the jaw bone cavity.

13. A dental prosthesis as defined in claim 12, wherein the second layer of biocompatible material comprises a matrix protein applied to the first layer of biocompatible material prior to insertion of the root portion of the dental prosthesis into the jaw bone cavity.

14. A dental prosthesis as defined in claim 12, wherein the first layer of biocompatible material comprises the layer of mineral trioxide aggregate.

15. A dental prosthesis as defined in claim 1,
   wherein the root portion of the dental prosthesis comprises a root main body portion and a root surface layer portion;
   wherein the root main body portion has the outer surface shape matching a three-dimensional undersized representation of the three-dimensional surface shape of corresponding outer surface portions of the root of the natural tooth of the pre-identified patient; and
   wherein the root surface layer portion comprises the biocompatible enhancement comprising a layer of biocompatible material abuttingly contacting the outer surface of the root main body portion and is shaped so that outer surface portions thereof dimensionally match the three-dimensional surface shape of corresponding outer surface portions of the root of the natural tooth of the pre-identified patient.

16. A dental prosthesis as defined in claim 15, wherein the layer of biocompatible material comprises the layer of mineral trioxide aggregate having a thickness of between 0.2 mm and 0.3 mm.

17. A dental prosthesis as defined in claim 1, wherein the biocompatible enhancement comprises a nano-crystalline diamond coating forming substantial portions of the outer surface of the root portion.

18. A dental prosthesis as defined in claim 1, the dental prosthesis further comprising:
   a permanent crown portion connected to the root portion of the dental prosthesis to form a unitary prosthetic structure;
   wherein the root portion comprises a primary body material;
   wherein the permanent crown portion comprises the primary body material; and
   wherein the root portion and the permanent crown portion together define the unitary prosthetic structure, the primary body material of the root portion of the unitary prosthetic structure and the primary body material of the permanent crown portion of the unitary prosthetic structure together comprising a substantial plurality of abuttingly contacting layers of material extending cross-sectionally through an extent of the prosthetic structure.

19. A dental prosthesis to be integrated into a jaw bone cavity of a pre-identified patient, the prosthesis being a finished manufactured product prior to its insertion into the jaw bone cavity, the prosthesis comprising:
   a root portion configured to be positioned in and integrated into a jaw bone cavity of a specific pre-identified patient and having an outer surface, the outer surface having a custom three-dimensional surface shape specifically dimensionally matching an undersized three-dimensional surface shape of corresponding outer surface portions of a root of a natural tooth of the pre-identified patient removed from the jaw bone cavity of the pre-identified patient, the root portion further comprising a biocompatible enhancement selected from the group comprising:
      a cured cement forming substantial portions of the outer surface of the root portion, the cured cement having a composition to enhance integration of the root portion into and adoption by a periodontal ligament cell structure within the jaw bone cavity receiving the root portion and being selected from the group consisting essentially of calcium hydroxide cement, glass-ionomer cement, resin-modified glass-ionomer cement, and light-activated resin-modified glass ionomer cement, and a layer of mineral trioxide aggregate forming substantial portions of the outer surface of the root portion.

20. A dental prosthesis as defined in claim 19, wherein the biocompatible enhancement comprises the layer of mineral trioxide aggregate forming substantial portions of the outer surface of the root portion.

21. A dental prosthesis as defined in claim 19, wherein the biocompatible enhancement further comprises one or more of the following:

ancestral cells located on the outer surface of the root portion immediately prior to and during final placement of the dental prosthesis into the jaw bone cavity, and portions of a natural tooth.

22. A dental prosthesis as defined in claim 19, wherein the biocompatible enhancement further comprises cells of a tooth.

23. A dental prosthesis as defined in claim 19, wherein the biocompatible enhancement further comprises a nano-crystalline diamond coating forming substantial portions of the outer surface of the root portion.

24. A dental prosthesis as defined in claim 19, wherein the biocompatible enhancement comprises the cured cement, the cured cement comprising the resin-modified glass-ionomer cement, the resin-modified glass-ionomer cement formed of a calcium alumino-silicate glass powder and an aqueous solution of an acrylic acid homo- or co-polymer.

25. A dental prosthesis as defined in claim 19, wherein the biocompatible enhancement comprises the cured cement, the cured cement comprising the light-activated resin-modified glass ionomer cement, activated prior to insertion into the root portion of the jaw bone cavity of the pre-identified patient.

* * * * *